(12) United States Patent
Haas et al.

(10) Patent No.: US 7,011,854 B2
(45) Date of Patent: Mar. 14, 2006

(54) METHOD FOR TREATING A MAMMAL BY ADMINISTRATION OF A COMPOUND HAVING THE ABILITY TO RELEASE CO, COMPOUNDS HAVING THE ABILITY TO RELEASE CO AND PHARMACEUTICAL COMPOSITIONS THEREOF

(75) Inventors: Werner Haas, Oeiras (PT); Carlos Romao, Lisboa (PT); Beatriz Roya, Oeiras (PT); Ana Cristina Fernandes, Amadora (PT); Isabel Goncalves, Oeiras (PT)

(73) Assignee: Alfama-Investigacao e Desenvolvimento de Produtos Farmaceuticos Lda, Oeiras (PT)

( * ) Notice: Subject to any disclaimer, the term of this patent is extended or adjusted under 35 U.S.C. 154(b) by 290 days.

(21) Appl. No.: 10/356,738

(22) Filed: Feb. 3, 2003

(65) Prior Publication Data

US 2004/0067261 A1    Apr. 8, 2004

Related U.S. Application Data

(60) Provisional application No. 60/353,233, filed on Feb. 4, 2002.

(51) Int. Cl.
  *A61K 31/555*    (2006.01)
  *A61K 31/28*    (2006.01)
  *A61K 31/295*    (2006.01)
  *A61K 31/30*    (2006.01)
  *A61P 29/00*    (2006.01)

(52) U.S. Cl. ............... 424/699; 424/450; 424/484; 424/488; 514/58; 514/141; 514/165; 514/184; 514/185; 514/186; 514/188; 514/189; 514/492; 514/501; 514/502; 514/505; 514/569; 514/605; 514/824; 514/825; 514/826; 514/879; 514/886; 514/887; 514/894; 514/903; 514/921; 514/950; 514/958; 514/959; 514/964

(58) Field of Classification Search ............... 424/450, 424/484, 488, 699; 514/58, 141, 165, 184–186, 514/188–189, 492, 501–502, 505, 569, 605, 514/824–826, 879, 886–887, 894, 903, 921, 514/950, 958, 959, 964
See application file for complete search history.

(56) References Cited

U.S. PATENT DOCUMENTS

| | | |
|---|---|---|
| 4,657,902 A | 4/1987 | Kappas et al. |
| 4,699,903 A | 10/1987 | Rideout et al. |
| 5,086,060 A | 2/1992 | Haley et al. |
| 5,102,670 A | 4/1992 | Abraham et al. |
| 5,447,939 A | 9/1995 | Glasky et al. |
| 5,621,000 A | 4/1997 | Arena et al. |
| 5,664,563 A | 9/1997 | Schroeder et al. |
| 5,670,664 A | 9/1997 | Kao et al. |
| 5,700,947 A | 12/1997 | Soldato |
| 5,861,426 A | 1/1999 | Del Soldato et al. |
| 5,882,674 A | 3/1999 | Herrmann et al. |
| 5,885,621 A | 3/1999 | Head et al. |
| 5,888,982 A | 3/1999 | Perrella et al. |
| 5,891,689 A | 4/1999 | Takle et al. |
| 6,040,341 A | 3/2000 | Del Soldato et al. |
| 6,051,576 A | 4/2000 | Ashton et al. |
| 6,066,333 A | 5/2000 | Willis et al. |
| 6,203,991 B1 | 3/2001 | Nabel et al. |
| 6,218,417 B1 | 4/2001 | Del Soldato |
| 6,242,432 B1 | 6/2001 | Del Soldato |
| 2002/0155166 A1 | 10/2002 | Choi et al. |

FOREIGN PATENT DOCUMENTS

| | | |
|---|---|---|
| WO | WO91/01128 | 2/1991 |
| WO | WO95/05814 | 3/1995 |
| WO | WO95/09831 | 4/1995 |
| WO | WO96/09038 | 3/1996 |
| WO | WO97/16405 | 5/1997 |
| WO | WO98/29115 | 7/1998 |
| WO | WO98/48848 | 11/1998 |
| WO | WO99/67231 | 12/1999 |
| WO | WO00/56743 | 9/2000 |
| WO | WO00/61537 | 10/2000 |
| WO | WO01/12584 | 2/2001 |
| WO | WO02/078684 | 10/2002 |
| WO | WO02/092072 | 11/2002 |
| WO | WO02/092075 | 11/2002 |
| WO | WO03/000114 | 1/2003 |

OTHER PUBLICATIONS

Chemical Abstracts 141:270758 (2004).*
Chemical Abstracts 140:40075 (2004).*
Chemical Abstracts 142:211995 (2004).*
Chemical Abstracts 137:119662 (2002).*
Choi et al., US Publication No. 2002 0155166 A1; Publication Date Oct. 24, 2002.
Motterelini et al.; Carbon Monoxide—Releasing Molecules Characterization of Biochemical and Vascular Activities; Circ. Res. 2002, 90:e17-e24.

(Continued)

*Primary Examiner*—John Pak
(74) *Attorney, Agent, or Firm*—Wilmer Cutler Pickering Hale and Dorr LLP

(57) ABSTRACT

Several classes of in vivo carbon monoxide-releasing compounds are useful for the treatment and/or prevention of diseases, such as chronic inflammatory, e.g., rheumatoid arthritis, and of diseases with a strong inflammatory component, such as atherosclerosis, stroke, coronary disease, and Alzheimers disease. The in vivo carbon monoxide-releasing compounds can be attached to known drug vectors and/or known anti-inflammatory drugs, such as aspirin.

14 Claims, No Drawings

OTHER PUBLICATIONS

Motterlini et al; Studies on the development of carbon monoxide-releasing molecules: potential applications for the treatment of cardiovascular dysfunction; CRC Press, New York, 2002; pp. 249-272—Rui Wang Editor.

Hans-Jochen Meder and Wolfgang Beck (1986) Metallkomplexe mit biologisch wichtigen liganden, XLII(1) carbonylmetallkomplexe mit anionen von mehrfunktionellen a-aminosaueren. Zeitschrift fuer Naturforschung 41b, 1247-1254.

Ivana Verona et al. (1996) Regloselectivity in the nucleophilic functionalization of dibenzofuran, dibezothiophene and xanthene complexes of Mn(CO)3+; Journal of Organometallic Chemistry 524, 71-80.

Clark et al.; (2003); Cardioprotective actions by a water-soluble carbon monoxide-releasing molecule; Circ. Res. 93:e2-8.

Johnson et al.; (2003) Metal carbonyls; a new class of pharmaceuticals; Angew Chem Int Ed Engl 42:722-3729.

Motterlini et al.; (2003) Bioactivity and pharmacologial actions of carbon monoxide-releasing molcules; Curr. Pharm Des 9:2525-2539.

Stanford et al. (2003) Heme oxygenase is expressed in human pulmonary artery smooth muscle where carbon momoxide has an anti-proliferative role; Eur. J. Pharmacol. 473:135-141.

Ozawa et al.; (2002) Leydig cell-derived heme-oxygenase-1 regulates apoptsis of premelotic germ cells in response to stress; J clin Invest 109:457-467.

Chauveau et al.; (2002) Gene transfer of heme oxygenase-1 and carbon monoxide delivery inhibit chronic rejection; Am J Transplant 2:582-592.

International Search Report in corresponding PCT application No. PCT/IB03/00932.

Otterbein Leo E et al; "Carbon Monoxide Has Anti-Inflammatory Effects Involving the Mitogen-Activated Protein Kinase Pathway" *Nature Medicine*; vol. 6, No. 4 (Apr. 2000), pp. 422-428.

* cited by examiner

METHOD FOR TREATING A MAMMAL BY ADMINISTRATION OF A COMPOUND HAVING THE ABILITY TO RELEASE CO, COMPOUNDS HAVING THE ABILITY TO RELEASE CO AND PHARMACEUTICAL COMPOSITIONS THEREOF

CROSS-REFERENCE TO RELATED APPLICATIONS

This application is based on and claims the benefit of U.S. Provisional Application No. 60/353,233, filed Feb. 4, 2002. The entire disclosure of this application is relied upon and incorporated by reference herein.

BACKGROUND OF THE INVENTION

The history of analgesic and anti-inflammatory medicines started with the use of decocted salicylate-containing plants by ancient Greek and Roman physicians. Willow bark was already used 300 BC for treating fever and pain. Sodium salicylate was introduced in 1875 as an antipyretic. At Bayer in Germany the less corrosive acetylsalicylic acid was synthesized and introduced into medicine in 1899 under the name of aspirin.

The impressive anti-inflammatory, analgesic and antipyretic effects of aspirin prompted researchers to develop a large number of related compounds most of which are organic acids. These compounds, referred to as aspirin-like drugs or nonsteroidal anti-inflammatory drugs (NSAIDs) are a heterogeneous group of substances which have no uniform chemical properties but share the same therapeutic effects as well as unwanted side effects. In 1971 Vane and colleagues have shown that aspirin and other NSAIDs inhibited the synthesis of prostaglandins. Prostaglandins serve many diverse functions throughout the body, with important roles in blood clotting, ovulation, initiation of labor, bone metabolism, nerve growth and development, wound healing, kidney function, blood vessel tone, and immune response (DuBois R. N. et al FASEB J. 1998, 12, 1063). Prostaglandins are produced locally in many different tissue types and have different local actions. PGE2 is generally thought to be the most important pro-inflammatory prostaglandin mediating tissue swelling, fever and hyperalgesia (heightened pain sensitivity). However, other prostanoids may be equally important. Prostacyclin (PGI2), for example, is likely to play an important role in the development of inflammatory pain (K. R. Bley, J. C. Hunter, R. M. Eglen and J. A. M. Smith; 1998, Trends in Pharmacological Science 19, 141–147). Another prostanoid, thromboxane, is produced by platelets and plays a crucial role in thrombotic events. The first enzyme in the prostaglandin synthetic pathway is fatty acid cyclooxygenase, which occurs in two forms, COX-1 and COX-2. COX-1 is constitutively expressed in many cells and tissues such as stomach, kidney and platelets, while COX-2 is induced at sites of injury by exogenous and endogenous inflammatory mediators. Aspirin acetylates serine residues in COX-1 and COX-2 thus resulting in irreversible inhibition of these enzymes. Other NSAIDs are reversible, competitive inhibitors of cyclooxygenases.

Because aspirin and other NSAIDs are organic acids and have a high capacity to bind to proteins, they accumulate in inflamed tissues, the GI mucosa, the renal cortex, the blood and in the bone marrow. These facts are well known and can be found in textbooks of Pharmacology such as Goodmann and Gilman's Pharmacological Basis Of Therapeutics, McGraw-Hill, New York Aspirin is rapidly deacetylated by the liver. However, COX-1 in platelets can be inhibited by low doses of aspirin in the portal circulation, thereby sparing COX-1 in endothelial cells and prostacylin synthesis (Benett 2001). NSAIDs are the most widely used drugs in the world; about 70 million people each day take prescribed NSAIDs, and about 200 million people each day take over-the-counter NSAIDs (Smith T. G. Rheum. Dis. Clin. North Am. 1998, 24, 501–523). In the United States 80 billion aspirin tablets are consumed annually (Flieger K. FDA Consum. January–February 1994) and about 50 million people spend $5–10 billion on NSAIDs each year (DuBois R. N. et al FASEB J. 1998, 12, 1063). Since the determination of these figures in 1999, it is most likely that the use of NSAIDs has further increased. Population studies have shown that 10–20% of all people who are 65 years or older are either currently receiving or have recently received a prescription for a nonsteroidal anti-inflammatory drug. During the next 20 years the number of people over 65 is expected to increase from 380 million to 600 million.

The frequent use of NSAIDs is based on the fact that it has many indications including mild headache, menstrual pain, fever, chronic polyarthritis, psoriatic arthritis, ankylosing spondylitis, osteoarthritis, gout, inflammatory soft tissue rheumatis, low back pain, postoperative and post-traumatic inflammation, thrombophlebitis and vasculitis (Juergen Steinmeyer, 2000, Arthritis Research 2, 379–385). In addition to the traditional use for the above indications, NSAIDs have been shown to be effective in the prevention of vascular disorders. Aspirin is the most widely used inhibitor of platelet function and is the standard against which other agents are judged. In the Antiplatelet Trialist Collaboration (46 trials with patients with acute myocardial infarction, prior myocardial infarction, unstable angina, stroke, or transient ischemic attack, aspirin reduced the long term risk of recurrent infarction, stroke, or death from a vascular cause by 25%. Aspirin acetylates COX-1 not only in platelets, but also in endothelial cells thereby preventing the synthesis of prostacyclin, a potent vasodilatator and platelet inhibitor. Despite the inhibition of prostacyclin, aspirin has a net anti-platelet effect by inhibiting thromboxane A2 synthesis in platelets (Benett 2001).

Not all biological effects of NSAIDs are related to the inhibition of cyclooxygenases. Other potential targets include nuclear receptors such as peroxisome proliferator activated receptor gamma and delta (PPAR γ and δ), kinases such as 1 kb kinase (IKKβ), and certain phosphodiesterases such as PDE5 and 2. Interactions of NSAIDs with such target depends on the structure and dose of the compound, and may have beneficial or adverse consequences.

NSAIDs are generally well tolerated; however, adverse reactions do occur in a small but important percentage of patients. Because of the very extensive use of NSAIDs this results in substantial morbidity and mortality. The most serious side effect of aspirin and related NSAIDs are gastrointestinal disorders, in particular the induction of gastroduodenal ulcers. Long term administration of aspirin also leads to a small increase in the number of hemorrhagic strokes. There is a dose dependent relationship to both complications. They can be minimized, but not eliminated, by administering the lowest effective dose of aspirin. The annual number of hospitalizations in the United States for serious gastrointestinal complications of NSAID use is at least 100,000 and the annual direct costs of such complications exceed U.S. $2 billion. The mortality rate among patients who are hospitalized for NSAID induced upper gastrointestinal bleeding is about 5 to 10% (for references to original articles see Wolke M. M., Lichtenstein D. R. and G. Singh, 1999; The New England Journal of Medicine 340, 1888–1899).

Extensive efforts have been made to prevent the adverse effects of NSAIDs. One strategy which has proven to be effective is to supplement NSAIDs medication with protective prostaglandin derivatives, such as misoprostol, or with a proton pump inhibitor, such as ranitidine. Another strategy is to modify NSAIDs themselves either to make them more selective or to add protective moieties. Safer NSAIDs have been developed, which selectively inhibit only the inducible cyclooxygenase, COX-2. The increased safety profile of selective COX-2 inhibitors is thought to be due to the fact that prostaglandins generated by COX-2 at the sites of injury cause tissue swelling, pain and inflammation, while those generated by COX-1 in the mucosa and by platelets have protective functions. Two selective COX-2 inhibitors, celcoxib (Celebrex®) and rofecoxib (Vioxx®) have become available and several related compounds are in early clinical development. Celecoxib and rofecoxib maintain selectivity for COX-2 even at high doses. It has been demonstrated in several clinical trials that these novel NSAIDs do cause less gastrointestinal complications than nonselective COX inhibitors.

Recent studies have shown that selective COX-2 inhibitors might open up a wide spectrum of new indications for NSAIDs. The degeneration of large areas of the brain in Alzheimer's disease is supposed to occur with the involvement of COX-2. Selective COX-2 inhibitors might also be directed towards the therapy of colorectal carcinomas. COX-2 expression is also increased in gastric and breast carcinomas, suggesting that selective COX-2 inhibitors might also be therapeutically useful for treating those tumours. Recently the US FDA approved the selective COX-2 inhibitor celecoxib for the treatment of the rare genetic disorder called familial adenomatous polyposis. Animal experiments have shown that COX-2 inhibitors inhibit angiogenesis and tumour growth in a dose dependent manner. COX-2 is expressed in the newly created blood vessels (especially in the endothelial cells) needed for tumour growth.

The advent of COX-2 selective compounds has motivated scientists to revisit the physiological and pathological role of the two known cyclooxygenase isozymes. These studies have revealed several potential disadvantages of cyclooxygenase inhibitors in general, and of selective COX-2 inhibitors in particular. While selective COX-2 inhibitors are effective in preventing colon cancer and possibly Alzheimers disease (Tocco G., Freire-Moar J. and Schreiber S. S.; 1997, Exp. Neurol 144, 339), they do not provide the prophylactic benefits of aspirin in vascular disease, which is largely, if not exclusively based on the reduction of COX-1 mediated thromboxane A2 synthesis in platelets. COX-2 was shown to have not only pro- but also anti-inflammatory properties (reviewed by P. R Colville-Nash and D. W. Gilroy; 2001, BioDrugs 15,1–9). In a crageenan induced pleurisy model in rats COX-2 first generated PGE2, which increased the transactivation function of NFkB and thereby upregulated the expression of many inflammatory mediators. At a later time point a shift occurred in which, by unknown mechanisms, PGE2 production was down regulated, while the production of cyclopentenone prostaglandins was increased. The "late" prostaglandins, which include PGD2 and its derivatives, in particular PGJ2, inhibit inflammation, at least in part by inhibiting NFkB signal transduction (A. Rossi, P. Kapahi, G. Natoli, T. Takahashi, Y. Chen, M. Karin and M. G. Saunter; 2000, Nature 403, 103–108).

These findings indicate that cycloxygenase inhibitors may delay the resolution of inflammation (see B. Poligone and A. S. Baldwin; 2001, The Journal of Biological Chemistry 276, 38658–64). Indeed cyclooxygenase inhibitors have been shown to delay gastric ulcer healing in mice (H. Mizunonet; 1997, Gastroeneterology 112, 387–397) and to exacerbate induced colitis in rats (A. Schmassmann, B. M. Peskar, C. Stettler, et al; 1998, Br. J. Pharmacology 123, 795–804; M. N. Ajuebor, A. Singh, and J. L. Wallace; 2000, Am J. Physiol. Gastrointest Liver Physiol 279, G238–44). In some patients treated with selective COX-2 inhibitors ulcers have progressed further to perforation.

A more recent study suggests that COX-2 mediated prostaglandin production is required for the generation of TGFβ producing regulatory T cells that mediate oral tolerance to dietary antigens (for references see 0. Morteau; 1999, Nature Medicine 5, 867–8). Sugawa and colleagues pointed out that COX-2 inhibitors may increase the production of leukotrienes, such as leukotriene B4 (LTB4), which is one of the most potent chemotactic/inflammatory factors (K. Sugawa, T. Uz, V. Kumar and H. Manev; 2000, Jpn J Pharmacol 82, 85). In chronically inflamed pulmonary tissue, NSAIDs lead to an increased production of leukotrienes and in this way to asthma-like reactions due to the inhibition of prostaglandin synthesis. COX-2 has also been reported to be involved in the regulation of the renin-angiotensin system, and to possess vasoactive anti-atherogenic properties (G. Dannhardt and W. Kiefer; 2001, European Journal of Medicinal Chemistry 36, 109–126). Based on these findings, COX-2 inhibitors might be expected to delay the resolution of inflammatory lesions and to exacerbate hypertension and atherocleosis. Thus, selective COX-2 inhibition is likely not to be the final triumph of the search for improved version of sodium salicylate, which began more than 100 years ago.

Another strategy to reduce the side effects of aspirin and aspirin-like drugs has been the attachment of NSAIDs with protective compounds. At least part of the toxicity of NSAIDs has been ascribed to their ability to bind to zwitterionic phospholipids, which provide the mucus gel layer with non-wettable properties. Preassociating NSAIDs with exogenous zwitterionic phospholipids prevented them from increasing the wettability of the mucus gel layer and protected rats against the injurious gastrointestinal side effects of these drugs, while enhancing their lipid permeability, anti-pyretic and anti-inflammatory activity (L. M. Lichtenberg, Z. M. Wang, J. J. Romero, C. Ulloa, J. C. Rerez, M. N. Giraud and J. C. Baretto, 1995, Nat Medicine 1, 154).

Another approach, which is currently in clinical testing, utilizes NSAIDs that are covalently derivatized with a nitric oxide (NO) releasing moiety (NO-NSAIDs). This strategy, which has been described in a series of patents (U.S. Pat. Nos. 5,621,100; 5,700,947; 5,861,426; 6,040,341; 6,218,417 B1; 6,218,417 B1; and 6,242,432) is based on the observation, that, NO has cytoprotective properties. In particular in the stomach, NO exhibits many of the same actions as prostaglandins, such as stimulation of mucus secretion and maintenance of mucosal blood flow. Indeed, NO-NSAIDs did not cause any gastrointestinal injuries in animals, and exhibited anti-inflammatory and analgesic effects, which exceeded those of the parent compounds (for references see P. del Soldato, R. Sorrentino and A. Pinto; 1999, Trends I Pharmacological Science 20, 319). The NO release from these compounds is a metabolic rather than a spontaneous process. The anti-inflammatory effects of these compounds are thought to be due in part to the inhibition of cyclooxygenases, and in part to the nitrosation and inactivation of caspase 1, an enzyme, that is required for the generation of at least two inflammation promoting cytokines, interleukin 1 and interleukin 18 (S. Fiorucci; 2001, Trends in Immunology 22, 232–235). Clinical studies must be undertaken to compare NO-NSAIDs and their parent drugs with regard to safety profile and therapeutic efficacy.

In contrast to COX-2 inhibitors nitro-aspirin is expected to retain or even surmount the prophylactic effect of aspirin in cardiovascular disease. One of the nitro-aspirin compounds, referred to as NC4016, inhibited arachidonic acid—stimulated aggregation of platelets at a concentration of 100 $\mu$M, whereas aspirin induced the same effect at 10 $\mu$M. However NC4016 was more efficient than aspirin in inhibiting platelet aggregation and adhesion induced by thrombin. The antithrombotic effect of NC4016 appears to be due at least in part to the release of NO, which results in increased cGMP levels in platelets, as well as to the inhibition of prostanoid synthesis.

Many diverse effects have been ascribed to endogenously produced NO and to therapeutically administered NO or NO donors. These include regulation of blood flow, maintenance of vascular tone, control of platelet aggregation, and various roles in the central and peripheral nervous system. The phenomenology described in the literature is rather complex. NO has been reported to have either pro- or anti-inflammatory effects (H. Kolb and V. Kolb-Bachofen; 1998, Immunology Today 19, 556) and pro- or anti-atherogenic effects (R. P. Patel, A. Levonen, J. H. Crawford, and V. M. Darley-smar; 2000, Cardiovascular Research 47, 465–74). Therefore, it is difficult to predict the long term effects of compounds, which exhibit sustained NO release.

There exists a need in the art for methods for preventing and/or treating diseases, for example, inflammatory diseases. In addition, there is a need for compounds and pharmaceutical compositions for preventing and/or treating diseases, for example, inflammatory diseases.

SUMMARY OF THE INVENTION

This invention aids in fulfilling these needs in the art by providing a method for preventing and/or treating a disease in a mammal, wherein said method comprises a step of administering to said mammal a compound having the capability to release carbon monoxide (CO) in vivo. The compound has the ability to release CO in vivo in a target site, for example in an inflammatory or pre-inflammatory site.

In preferred embodiments, the method is used for preventing and/or treating inflammatory disease or disease with a strong inflammatory component, asthma, injury, infarction, circulatory disease.

As used herein, a target site means a site where a therapeutic effect is expected by use of a compound of the invention. Such therapeutic effect can be obtained at least partly by means of the released CO as active principle.

Thus, a compound for use in the method according to the invention is characterized in that it comprises at least one CO-releasing moiety.

As used herein, a CO-releasing moiety means a moiety having the ability to release carbon monoxide in vivo. Examples of such moieties are moieties containing CO and include a moiety that comprises of CO. Other examples of CO-releasing moieties are moieties capable of generating CO. CO can be released in certain conditions (e.g. oxidative conditions of a targeted pre-inflammatory or inflammatory site.)

In a particular embodiment, the CO-releasing moiety is linked to a second moiety. This second moiety is, for example, a drug carrier and/or a therapeutic agent such as, for instance, an anti-inflammatory agent. It may be selected depending on its known capacity to target the site/tissue in which a therapeutic effect is expected. For example, an-anti-inflammatory agent can be selected for its known capacity to accumulate in an inflammatory lesion.

Anti-inflammatory drugs, which accumulate in inflamed tissues, include aspirin, indomethacin, nimesulide, vioxx, celecoxib and other nonsteroidal anti-inflammatory drugs that are organic acids.

The CO releasing moiety may also be targeted to bones by using biphosphonates as carriers.

The CO releasing moiety may also be targeted to any particular tissue or cell type by using proteins as carrier. Carrier proteins include but are not limited to antibodies which are specific for a cell surface protein or a component of the extracellular matrix.

In a preferred embodiment of the invention, the compound having the ability to release carbon monoxide in vivo is a compound from one of the following classes:

Class 1—CO containing organometallic complex. Such a compound can be dissolved in physiologically compatible support.

Class 2—CO containing organometallic complex linked to at least another pharmacologically important molecule. For example, said pharmacologically important molecule is a carrier, a drug (e.g., an anti-inflammatory agent). Furthermore, the CO containing organometallic complex and the at least other pharmacologically important molecule are optionally linked by means of an appropriate spacer.

Class 3—Supramolecule aggregates made of CO containing organometallic complexes optionally encapsulated e.g. in a cyclodextrin host and/or another appropriate inorganic or organic support.

Class 4—CO containing inorganic complex bearing ligands, e.g., polidentate ligands, containing N and/or S donors that function as reversible CO carriers.

Class 5—CO containing inorganic complex bearing ligands, e.g. polidentate ligands, containing N and/or S donors that function as reversible CO carriers, linked to at least another pharmacologically important molecule. For example, the pharmacologically important molecule is a carrier, a drug, (e.g. an anti-inflammatory agent). Furthermore, the CO containing organometallic complex and the at least other pharmacologically important molecule are optionally linked by means of an appropriate spacer.

Class 6—Organic substances that release CO either by an enzymatic process or by decarbonylation. Such a compound can be dissolved in physiologically compatible supports.

Class 7—Organic substances that release CO either by an enzymatic process or by decarbonylation, e.g., dichloromethane optionally encapsulated either in cyclodextrin hosts and/or other appropriate inorganic or organic supports.

This invention also provides a pharmaceutical composition, which comprises a compound of the invention having the ability to release carbon monoxide in vivo. In a preferred embodiment, the pharmaceutical composition can be used for preventing and/or treating inflammatory diseases. In one embodiment of the invention, the inflammatory disease is a chronic inflammatory disease, such as rheumatoid arthritis. In another embodiment, the pharmaceutical composition can be used for preventing and/or treating asthma injury, infarction, circulatory disease.

In one embodiment, the method for preventing and/or treating a disease in a mammal according to the invention comprises a step of administering to said mammal a pharmaceutical composition of the invention. The method comprises administering a pharmaceutical composition of the invention to a mammal, such as humans, and various animal species, including cats, dogs, cows, pigs, horses, sheep, and goats. In a preferred embodiment, this invention provides a method for preventing and/or treating inflammatory disease, e.g. chronic inflammatory disease, such as rheumatoid arthritis.

DETAILED DESCRIPTION OF THE INVENTION

The present invention describes several classes of compounds designed to release carbon monoxide (CO) in vivo. This invention is based on recent evidence that carbon monoxide is an endogenous mediator that has anti-inflammatory and anti-thrombotic properties. Carbon monoxide has long been known to inhibit human platelet aggregation (Brune and Ullrich, 1987, Mol Pharmacol 32, 497). Within the past decade observations have accumulated which suggest that CO is an endogenous mediator of a variety of physiological processes. CO was shown to cause vasodilation (Sammut et al, 1998, British Journal of Pharmacology 125, 1437), to support graft survival in allogeneic or xenogeneic hosts (Soares et al 1998, Nature Medicine 4, 1073), and to ameliorate inflammatory reactions (Otterbein et al, 2000, Nature Medicine 6, 422). Carbon monoxide (CO) is a diatomic, diffusible, colorless gas. The principal advantage of CO as a mediator of therapeutic and preventive measures is its stability and limited reactivity. The biological effects of CO do not depend on the formation of intermediary, more stable mediators. The potential of CO-releasing compounds in therapeutic and prophylactic medicine will become apparent from the following brief review of the known facts about CO and of its role in physiological and pathological processes.

In the body, generation of CO requires heme oxygenase. The enzyme was initially found to be involved in the degradation of heme in aging red blood cells. It carries out the oxidation of the heme molecule (Fe-protoporphyrin IX) in concert with oxygen and NADPH-cytochrome P450 reductase. Heme oxygenase is induced by heme, enabling it to respond to hemolysis or tissue destruction, which releases heme from hemoglobin of erythrocytes and from mitochondrial enzymes of nucleated cells, respectively. The products of the catalytic degradation of heme are CO, ferric iron, and bilirubin, which is rapidly converted into biliverdin. Thus, heme oxygenase serves catabolic and anabolic functions within cells. In its catabolic function it downregulates cellular heme and hemoprotein levels and thereby inactivates the most effective catalyst for the formation of free radicals, the heme molecule. In its anabolic role, heme oxygenase produces bile pigments, CO, and iron, all of which are biologically active. The bile pigments bilirubin and biliverdin function as anti-oxidants. Iron regulates expression of various genes, including that of HO-1 itself, as well as transferin receptors, ferritin, and NO synthase. Most important with respect to the present invention is the third product, carbon monoxide (CO), which acts as a signal transducer.

Heme is not only the only known source of CO in the body, it is also the only known target. In physiological systems, heme is bound to certain proteins, which bind oxygen at the site of the iron atom or function as components of the membrane bound electron transport system. Cellular respiration, energy generation, and chemical oxidations are dependent on these heme proteins. Heme proteins include hemoglobin, myoglobin, catalase, cytochrome b5, all cytochrome P450s, tryptophan pyrrolase, NO synthetase isozymes, and soluble guanylate cyclase (sGC). The latter enzyme is the best characterized mediator of the biological effects of NO and CO. Binding of NO to the prosthetic heme group of sGC activates the enzyme to generate guanosine 3',5'-monophosphate (cyclic GMP or cGMP). cGMP in turn activates one or more protein kinases, at least some of which phosphorylate proteins that are involved in Ca++ flux. CO is a much weaker activator of purified sGC in vitro than NO. However, attachment of a small molecular weight compound referred to as YC-1, and possibly of an as yet unknown, endogenous cofactor, dramatically increases the sensitivity of the enzyme to its activation by CO. Cyclic GMP is degraded and thus inactivated by several phosphodiesterases, which exhibit a tissue specific expression pattern. Thus NO and CO mediated signal transduction is under the control of NO and CO generating enzymes, as well as cGMP inactivating phosphodiesterases. In the context of the present invention it is important to note that the cGMP mediated effects of CO releasing compounds can be augmented by attaching such compounds to known phosphodiesterase inhibitors (see below). Because of the tissue specific expression of phosphodiesterases (PDEs), this strategy allows to target the effect of released CO to particular tissues.

PDE3 and PDE4 isozymes, for example, are expressed in the airway, vascular smooth muscle cells, heart, liver, endothelial cells, monocytes and T cells. PDE4 isozymes are in addition expressed in the brain, platelets, neutrophils, eosinophils and mast cells (Conti M. and Jin L.; 1999, Progr Nucleic Acid Res. Mol. Biol. 63, 1–38) and PDE7 is inducible in T cells (Li L., Yee C., and Beavo J. A.; 1999, Science 283, 848–851). The effect of CO may be augmented in specific cell types by the concomitant inhibition of one or a set of PDEs. A particularly strong augmenting effect can be expected if the CO-releasing moiety is attached to inhibitors of cGMP selective PDEs.

Many of the biological effects of CO have been revealed through studies of the heme oxygenases (HOs). Three isoforms of heme oxygenases are known, HO-1, HO-2, and HO-3. HO-1 (also known as heat shock protein 32 or HsP32) is induced not only by heme, but by a large variety of exogenous and endogenous agents, which induce inflammatory responses or which are present in pathological conditions with a strong inflammatory component, such as atherosclerosis or Alzheimer's disease. HO-1 deficient mice develop an anemia associated with low serum iron levels. Iron accumulates in particular in the kidney and the liver leading to oxidative damage, tissue injury, and chronic inflammation (K. D. Poss and S. Tonegawa; 1997, Proc. Natl. Acad. Sci. USA 94, 10919–10924).

HO-2 is constitutively expressed in all cell types, and its expression is not affected by the stimuli, which induce HO-1. The only known regulator of HO-2 yet identified is adrenal glucocorticoid. HO-2 is a hemoprotein with two putative heme regulatory motifs (HRMs) and one site being the 24-residue conserved "heme pocket" catalytic domain. Heme, in particular in its protein bound form, activates molecular oxygen and forms reactive oxygen radicals. Thus, HO-2 may function as a heme sensor and as such serve as a regulator of heme-responsive genes, including the gene that encodes HO-1. The oxygen radical generating function of HO-2 is thought to have a physiological role in sperm cells, which depend on hydroxyl radicals for function. HO-2 is expressed in the central and peripheral nervous system at various sites. The deletion of the HO-2 gene revealed an important function of HO-2 and its product, CO, in nonadrenergic, noncholinergic (NANC) transmission in myenteric ganglia. Studies with HO inhibitors depleted cGMP levels in olfactory neurons suggested a neurotransmitter function of CO in these cells (reviewed by D. E. Baranano and S. H. Snyder; 2001, Proc. Natl. Acad. Sci. USA 98, 10996–11002).

HO-3 transcripts are found in the spleen, liver, thymus, prostate, heart, kidney, brain and testis. This isoform has only negligible enzymatic activity. It has two putative heme binding sites and is thought to have a regulatory role in heme dependent, cellular processes.

Within the last 5 years many studies have demonstrated protective effects of CO in a variety of disease models in animals. Lipopolysaccharide (LPS), a constituent of the gram-negative bacterial cell wall, is a potent inducer of inflammation. L. Otterbein and colleagues have shown in vitro using murine macrophages, and in vivo in mice, that CO at low concentrations inhibited the LPS induced production of two pro-inflammatory cytokines, tumor necrosis factor-$\alpha$ and interleukin 1-$\beta$, but increased the production of the anti-inflammatory cytokine interleukin 10 (L. E. Otterbein, F. H. Bach, J. Alam, M. Soares, H. T. Lu, M. Wysk, R. J. Davis, R. A. Flavell and A. M. K. Choi; 2000, Nature Medicine 6, 422–428).

Fujita and colleagues studied the effects of CO in a model of lung injury induced by ischemia/reperfusion in mice. HO-1 deficient mice died from ischemic lung injury, but could be rescued by inhaled CO. The beneficial effect of CO was shown to be due to the reduction of platelet adhesion, an increase in the microcirculatory blood flow and the inhibition of expression of plasminogen activator inhibitor 1 (PAI-1), thereby enhancing fibrinolysis and reducing intravascular thrombosis. It should be noted that inhalation of only 65 p.p.m. NO was as effective in reducing mortality as inhalation of 500–1000 p.p.m. CO. (T. Fujita, K. Toda, A. Karimova, S-F. Yan, Y. Naka, S-F. Yet and D. J. Pinsky; 2001, Nature Medicine 7, 598–604).

Using a similar model in rats, Otterbein and colleagues demonstrated that CO inhalation reduced neutrophil infiltration and lung injury and increased survival of the animals. The therapeutic effects were achieved with CO concentrations far less than the toxic concentrations and even less than the concentrations used in human pulmonary function tests. (L. E. Otterbein, L. L. Mantell and A. M. K. Choi; 1999, Lung Cell. Mol. Physiol. 20, L688-L694). Already in 1987, B. Brune and V. Ullrich showed that CO inhibits platelet aggregation (B. Brune and V. Ullrich; 1987, Mol. Pharmacol. 32, 497–504). A study by Steiner and colleagues indicates that CO has an anti-hyperalgesic effect in inflamed paws of rats (A. A. Steiner, L. G. Branco, F. Q. Cunha, and S. H. Ferreira; 2000, Br. J. Pharmacol. 132, 1673–1682). Several recent studies demonstrate striking effects of HO-1 and CO on blood vessels, endothelial cells, and vascular smooth muscle cells. Duckers and colleagues using gene transfer and gene knock out techniques demonstrated a protective role of HO-1 expression in arterial wound repair. HO-1 effects mediated fully or in part by its product CO included inhibition of vasoconstriction and inhibition of smooth muscle cell proliferation (H.,J. Duckers, M. Boehm, A. L. True, S-F Yet, H. San, J. L. Park, R. C. Webb, M-E. Lee, G. J. Nabel and E. G. Nabel; 2001, Nature Medicine 7, 693–698). Togane and colleagues demonstrated that CO inhibits vascular smooth muscle cell proliferation and neointimal formation after ballon injury (T Y. Togane, T. Morita, M. Suematsu, J. I. Yamazaki, and S. Katayama; 2000, Am. J. Physiol. Heart Circ. Physiol. 278, H623–632). Several groups demonstrated that low concentrations of CO prevent endothelial cell death (see for example S. Brouard, L. E. Otterbein, F. Anrather, E. Tobiasch, F. H. Bach, A. M. K. Choi, and M. P. Soares; 2000, J. Exp. Med. 192, 1015–1025). M. Soares and colleagues also have shown that expression of HO-1 is essential for the survival of xenotransplants. Mouse hearts transplanted to rats survive long term if the recipients are treated with cobra venom factor and cyclosporin. Inhibition of hemoxygenase by tin protoporphyrin caused acute rejection in 3–7 days. The rejection was associated with platelet aggregation, thrombosis of coronary arterioles, myocardial infarction, and apoptosis of endothelial cells and cardiac myocytes. These injuries to the graft and its rejection were prevented by exposing the recipients to air containing 400 p.p.m. CO (K. Sato, J. Balla, L. Otterbein et al; 2001, J. Immunology 166, 4185–4194).

The above-described findings suggest that hemoxygenases are potential targets for drugs that are useful in a variety of pathological conditions. Drug candidates include compounds that induce or inhibit the expression of HO-1, and compounds that inhibit or augment the catalytic activity of hemoxygenases. Inhibitors of HO-1 expression or of its enzymatic activity may be useful for treating pathological conditions that are mediated at least in part by excessive amounts of either one of the three hemoxygenase products, CO, bilirubin, and iron. Endotoxin shock is induced by bacterial cell wall derived lipopolysaccharides (LPS, also known as endotoxin). LPS induced HO-1 generates CO, which may contribute to the reduction in vascular tone during sepsis. U.S. Pat. No. 5,888,982 describes strategies that aim to inhibit sepsis induced hypotension by inhibitors of HO-1 transcription, such as anti-sense oligonucleotides, and/or by inhibitors of the enzymatic activity of hemoxygenases. Hemoxygenase inhibitors, which block the binding of heme to hemeoxygenases may also be used to reduce heme catabolism thereby preventing the release of iron and bilirubin, and increasing the rate at which heme and iron are excreted into the intestine. Such compounds including tin mesoporphyrin (SnMP, U.S. Pat. No. 4,657,902) and diidodeuteroporphyrin (Snl2DP, U.S. Pat. No. 4,699,903) may be used for treating neonatal hyperbilirubinemia and other conditions associated with toxic bilirubin levels such as various forms of anemias and liver diseases. Hemeoxygenase inhibitors have also been proposed for the treatment of immunsuppressed patients, for example for treatment of AIDS patients (U.S. Pat. No. 6,066,333). Compounds that induce the expression and/or augment the enzymatic activity of hemoxygenases are useful for treating chronic inflammatory diseases, asthma, injury, atherosclerosis and infarction. Hemoxygenase inducers described in U.S. Pat. No. 6,066, 333 include prostaglandins of the A series, vitamin B12, hemin, hemin derivatives, and compounds that decrease nitric oxide synthesis. Heme-bearing microparticles have been proposed to be used for the targeted delivery of drugs to heme receptor bearing cells in the liver for the treatment of viral hepatitis and hepatoma (U.S. Pat. No. 5,891,689). Such compounds may induce HO-1 expression. Therapeutic HO-1 expression could also be achieved by gene transfer as described in U.S. Pat. No. 6,203,991. The above described strategies aiming to augment HO-1 activity are complicated by the fact that hemoxygenases not only generate CO, but also two potentially toxic compounds, bilirubin and iron.

Alternatively, CO could be administered as a gas, for example by a pneumatic system as described in U.S. Pat. No. 5,664,563 or by local applications, for example, to stented coronary arteries or to organs before transplantation. Gaseous CO has been evaluated as a therapeutic agent long before its endogenous mediator function has been recognized. More than 25 years ago Beutler administered CO at a concentration of 1000–2000 p.p.m. to two sickle cell disease patients. In both patients, significant anti-sickling effects and prolongation of red cell survival was observed. Beutler did not recommend CO as a treatment for sickle cell disease, but suggested that further trials should be conducted under carefully controlled conditions (E. Beutler; 1975, Blood 46, 253–259). In a more recent comment on the beneficial effects of CO inhalation in a lung ischemia/reperfusion model in rodents, Thiemermann was not in favor of CO inhalation therapy of patients, as he believes that the dangers of CO inhalation outweigh the benefits (C. Thiemermann; 2001, Nature Medicine 7, 535–536). Nevertheless, it is conceivable, that gaseous CO could be useful for a number of clinical applications, such as organ transplantation or ischemic lung injury (see above).

The present invention represents a novel strategy, namely, the use of compounds, which exhibit therapeutic effects fully or in part by the generation of free carbon monoxide (CO). Carbon monoxide is generated from precursor compounds either by spontaneous release or by a metabolic process (i.e. with the involvement of one or more enzymes).

As used herein, the term "spontaneous release" means thermally, chemically, oxydatively induced release and also in some cases, such as in photodynamic therapy conditions, release by reactions induced by light. The release of CO from the compound is immediately assisted by donor molecules which are ubiquitous and unavoidable in the organism, from water to proteins or nucleotides.

As used herein, the term "release by metabolic process" means release with the involvement of one or more enzymes such as, for example, cytochrome P450 and glutathione S-transferase. The preferred embodiments of this invention are compounds comprising two components, a CO releasing moiety, and a second pharmaceutically important molecule e.g., a known drug carrier, and/or a known anti-inflammatory agent. A preferred class of conjugation partners for the CO-donors are nonsteroidal anti-inflammatory drugs (NSAIDs), including but not limited to aspirin. These drugs are known to accumulate in inflammatory lesions. CO-donors can also be attached to other anti-inflammatory agents, including but not limited to steroids and inhibitors of phosphodiesterases (PDE), in particular inhibitors of PDE4.

Delivery of CO in vivo to target tissues such as injured blood vessels or inflammatory lesions, is safe and beneficial in a large variety of diseases. Diseases that can be treated by CO donors are chronic inflammatory diseases, including, but not limited to, rheumatoid arthritis, multiple sclerosis, and other diseases with a strong inflammatory component, including but not limited to stroke, Alzheimers disease, atherosclerosis, coronary atherosclerosis, transplantation associated atherosclerosis, or restenosis after coronary stent implantation. In many indications, in particular those related to atherosclerosis and Alzheimer's disease, the compounds are useful for prevention.

Although the present invention comprises a number of different classes of compounds, the active principle in each case is carbon monoxide (CO), which acts alone or in conjunction with those moieties of the herein disclosed compounds that remain after the release of CO. Thus, according to the terminology used herein, a herein disclosed compound is modified, after administration to a mammal, into CO (product 1) and at least one other compound (product 2) which may or may not have pharmacological effects. In a preferred embodiment of the herein disclosed compounds, the herein disclosed compounds give rise, after administration to a mammal, to CO and product 2 which is identical with or closely related to known drugs or compounds with known pharmacological effects. Product 2 may be identical with or closely related to a known drug which has anti-inflammatory effects by interacting with a nuclear receptor, or a G protein coupled receptor, or a cyclooxygenase, or a phosphodiesterase. Examples of product 2 are aspirin, indomethacin, nimesulide, piroxicam, flurbiprofen, meloxicam, naproxen, vioxx, celecoxib and other cyclooxygenase inhibitors. Further examples of product 2 are compounds that are identical or closely related to cortisol, prednisolon, dexamethason, betamethasone, dehydroepiandrosterone (DHEA) or estradiol, diethylstilbestrol (DES), tamoxifen or other selective estrogen receptor modulators (SERMs), 1,25 dihroxyvitamin D, troglitazone or other thiazolidinediones (TZDs), or cyclopentenones. Further examples of product 2 are compounds identical with or closely related to pentoxifylline, rolipram or other phosphodiesterase inhibitors. Still other examples of product 2 are alendrolate or other biphosphonates. CO (product 1) may complement, or augment, or inhibit pharmacological effects of product 2. In some cases, CO can decrease adverse effects of product 2, which limit their therapeutic applicability when used alone, without the CO-releasing moiety. CO is generated either by spontaneous release or by metabolic process.

It is well known that CO is toxic when it reaches high levels in the environment and in the blood. The toxicity of CO is due to its ability to bind to the heme group of hemoglobin, the oxygen-carrying molecule in human blood. Hemoglobin that is associated with CO is referred to as carboxyhemoglobin or COHb. Because CO's affinity to bind with hemoglobin is 250 times greater than that of oxygen, relatively low airborne concentrations and long exposure times can result in substantial COHb concentrations in the blood. As COHb levels increase, less hemoglobin is available for the transport of oxygen. The acute health effects of CO exposure are headache, dizziness, decreased vigilance, decreased hand-eye coordination, weakness, confusion, disorientation, lethargy, chest pain (incardica patients), nausea, and visual disturbances. The severity of the symptoms depends mainly on the concentration of CO and the length of exposure time. COHb saturations of 0.5% to 3% can be found in nonsmoking adults and levels of 5 to 6% have been reported in smokers and in patients with hemolytic anemias. The symptoms of CO poisoning are usually only seen at COHb levels above 10%. Common sources of toxic CO levels in the environment are exhausts of internal combustion engines, gas water heaters and gas fires that are improperly vented.

Another source of CO intoxication is dichloromethane (DCM) also referred to as methylene chloride. DCM is a dense, colorless organic solvent. It has a mild, sweet odor, and evaporates very quickly. It is widely used as a paint stripper and is also a component of certain aerosols and pesticide products and is used in the manufacture of photographic films. DCM may enter the body when it is inhaled or ingested. It is readily absorbed through body membranes (e.g. stomach, intestine and lungs) and quickly enters the blood stream. Cytochrome P-450 and gluthatione S-transferase enzymes can both metabolize DCM to carbon monoxide or carbon dioxide. If DCM is breathed at levels above 500 ppm (500 parts per million parts air), it may cause effects much like those produced by CO poisoning. Extensive studies have been conducted on the toxicity, carcinogeneicity, and teratogenicity of DCM. Studies with rodents suggest that frequent exposure to DCM can cause changes in liver and kidney. However, studies of DCM exposed workers indicate that it is unlikely that DCM will cause serious liver or kidney damage in humans unless exposure is very high (Agency for Toxic Substances and Disease registry, Division of Toxicology, Atlanta, Ga., USA). Some rats and mice exposed to high concentrations of DCM throughout their lifetime developed cancer. However, DCM has not been shown to cause cancer in humans exposed at occupational levels. Teratology studies in mice and rats examined the effect of exposure to 1250 ppm DCM in the atmosphere, 7 hours per day on 6 to 15 days of gestation. No material or foetal toxicity attributable to the DCM exposure was reported (Schwetz et al 1975; Toxicol Appl. Pharmacol. 32, 84). The occupational Health and Safety Administration (OSHA 1991) has established exposure limits for persons who work with DCM. These include an 8-hr time-weighted average (TWA) of 25 ppm and an acceptable maximum peak above the ceiling of 125 ppm (5 minutes in any 2 hours) in the workplace air. In 1976, The National Institute for Occupational Safety and Health (NIOH 1976) recommended a 10-hour TWA exposure limit of 261 milligrams per cubic meter (75 ppm) and a 1,737 milligrams per cubic meter (500 ppm) peak (15-minute sampling) in the presence of CO concentrations less than or equal to 9.9 ppm.

One active principle of all compounds described in this invention is CO, and some are related to DCM. However, the above described toxicity of CO and DCM occurs at levels that are far above the levels required to achieve therapeutic and prophylactic effects. Moreover, the CO-releasing moieties described here are designed to release CO at specific sites in the body, such as inflamed tissues or pre-atherosclerotic lesions of arteries. Some of the CO-releasing moieties herein described accumulate in inflammatory lesions much like aspirin and many of the known NSAIDs. Others are targeted to specific tissues, e.g. bones in the case of biphosphonate derivatives. Again others preferentially release CO in the presence of reactive oxygen species that are known to be generated at inflammatory sites and in atherosclerotic lesions. Development of the compounds described in the present invention for clinical applications will greatly benefit from the extensive work that has previously been done on CO and DCM toxicology.

Based on the above considerations, this invention provides compounds that can deliver CO in vivo to living tissues, undergoing inflammatory processes for instance. The present invention provides a number of different chemical systems that enable this purpose to be achieved. Preferred chemical systems are for example:

Class 1—CO containing organometallic complexes dissolved in physiologically compatible support.

Class 2—CO containing organometallic complex linked to at least another pharmacologically important molecule. For example, said pharmacologically important molecule is a carrier, a drug (e.g., an anti-inflammatory agent). Furthermore, the CO containing organometallic complex and the at least another pharmacologically important molecule are optionally linked by means of an appropriate spacer.

Class 3—Supramolecule aggregates made of CO containing organometallic complexes encapsulated in cyclodextrin hosts and/or other appropriate inorganic or organic supports.

Class 4—CO containing inorganic complexes bearing several categories of polidentate ligands containing N and/or S donors that function as reversible CO carriers.

Class 5—CO containing inorganic complex bearing ligands, e.g. polidentate ligands, containing N and/or S donors that function as reversible CO carriers, linked to at least another pharmacologically important molecule. For example, said pharmacologically important molecule is a carrier, a drug, (e.g. an anti-inflammatory agent). Furthermore, the CO containing organometallic complex and the at least another pharmacologically important molecule are optionally linked by means of an appropriate spacer.

Class 6—Organic substances that release CO either by an enzymatic process or by decarbonylation, dissolved in physiologically compatible supports.

Class 7—Organic substances that release CO either by an enzymatic process or by decarbonylation, e.g., dichloromethane, encapsulated either in cyclodextrin hosts and/or other appropriate inorganic or organic supports.

The following sections describe the guidelines for selecting these classes of compounds and provide specific examples.

Use of Organometallic Complexes for the Delivery of CO to Inflammated Tissues.

The role of transition metal complexes in medicine has been well recognized by many investigators and is presently undergoing a steady expansion. [C. Orvig, M. J. Abrams, Chem. Rev. 1999, 99, 2201 and following articles] Anti-carcinogenic, metal-based drugs are among the best known, in particularly the platinum derivatives, such as cis-platin and carboplatin. [E. Wong, C. M. Giandomenico, Chem. Rev. 1999, 99, 2451; E. R. Jamieson, S. J. Lippard, Chem. Rev. 1999, 99, 2467; J. Reedijk, Chem. Rev. 1999, 99, 2499]. The development of medical applications for organometallic complexes has been slower, but important advances have been made using the two best and longer established families of organometallic complexes known: the metallocenes and the carbonyls. Anti-carcinogenic properties have been found for several metallocenes, the best example being that of titanocene dichloride [M. J. Clarke, F. Zhu, D. R. Frasca, Chem. Rev. 1999, 99, 2511]. With respect to the transition metal carbonyls that concern the present invention research has progressed more slowly. Carbonyl complexes of transition metals have been known for a long time and their derivatives have been widely studied both in fundamental organometallic chemistry and in a multitude of catalytic applications. The discovery of the first of such carbonyls, $Ni(CO)_4$ by C. Langer and L. Mond in 1888 led to the industrial process of Ni purification (the Mond process) which, requires very careful operation and safety procedures in order to deal with the very noxious and toxic nature of $Ni(CO)_4$. [W. E. Trout, Jr. J. Chem. Ed. 1938, 77]. The toxicity of these compounds well surpasses that of CO alone. Of course, CO is a well recognized toxic molecule, which is able to block the metal centers of hemeproteins, like hemoglobin and others. [E. Di Cera, M. L. Doyle, P. R. Connelly, S. J. Jill, Biochemistry, 1987, 26, 6494] Toxicity of a series of Cr, Mn, Fe and Ni organometallic carbonyls has been studied in mice and rats. The effects observed included selective necrosis of the nonconciliated bronchiolar epithelial (Clara) cells and other deleterious effects within 24 h of administration. [W. M. Haschek, P. J. Hakkinen, H. P. Witschi, R. P. Hanzlik, G. J. Traiger, Toxicol. Lett. 1982, 14, 85]. However, iron carbonyls can be used in human diets as iron supplements. These compounds have been shown to have a high bioavailability as measured by hemoglobin repletion in iron-deficient rats. [P. V. Sacks, D. N. Houchin, Am. J. Clin. Nutr. 1978, 31, 566]. Later studies emphasize the low toxicity of iron carbonyl powder and its absorption by the intestinal mucosa in rats, [H. A. Hubers, G. M. Brittenham, E. Csiba, C. A. Finch, J. Lab. Clin. Med. 1986, 108, 473] and reveal its usefulness and advantage over inorganic iron salts in the treatment of anemias in humans, which are caused by iron deficiency. [V. R. Gordeuk, G. M. Brittenham, C. E. McLaren, M. A. Hughes, J L. J. Keating, Blood, 1986, 67, 745].

U.S. Pat. No. 5,086,060 claims the use of iron carbonyl derivatives of several polyene molecules for the treatment of acne and psoriasis. However, more extensive investigations of the biological applications of organometallic carbonyls only started in the late 1980's with the work of Jaouen, Vessières and their co-workers, on the development of organometallic reagents for immunoassay procedures, the so-called carbonylmetalloimmunoassay (CMIA). [G. Jaouen, A. Veesières, I. S. Butler, Acc. Chem. Res., 1993, 26, 361] These studies led to several successive discoveries that are related to the applications of organometallic compounds to biological systems, leading to a new area of Bio-organometallic Chemistry. Recent applications include the development of new molecules not only for immunoassays but also for radiopharmaceutical, radiotherapeutic, imaging and other purposes, including bioactive molecules and markers. [K. Severin, R. Bergs, W. Beck, Angew. Chgem. Int. Ed. 1998, 37, 1634; N. Metzler.Nolte, Angew. Chem. Int. Ed. 2001, 40, 1040; G. Jaouen, S. Top, A. Vessières, R. Alberto, J. Organomet. Chem. 2000, 600, 23]. Carbonyl containing derivatives have proven very valuable and flexible in their uses. Their stability and compatibility with physiological media has been shown to be adequate for both in vitro and in vivo applications. These observations are of great interest for medicinal chemists, who generally regarded metal carbonyls to be too toxic for biological, and in particular clinical applications.

Indeed, very recent research on metal containing enzymes revealed the unexpected role of carbonyl complexes in nature, and some enzymes have been found to contain M-CO bonds in their active sites. Examples of such enzymes are the iron-nickel hydrogenase and the iron only hydrogenase [M. Frey, J. C. Fontecilla-Camps, A. Volbeda, in Handbook of Metalloproteins, A. Messerschmidt, R. Huber, T. Poulos, K. Wieghardt Eds. J. Wiley and Sons Ltd., 2001, 880; B. J. Lemon, J. W. Peters, ibidem p. 738].

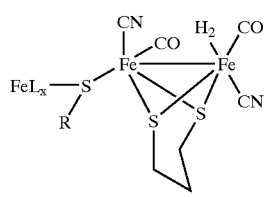

Desulfovibrio desulfuricans

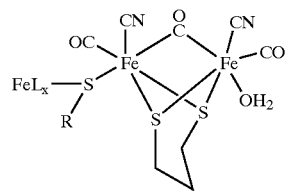

Clostridium pasteurianum

CO dehydrogenases carry out the oxidation of CO to $CO_2$ plus 2 electrons and $2H^+$. Two of these enzymes have also been structurally characterized. They contain Cu and Ni in their active centers and involve intermediate M-CO species [H. Dobbek, L. Gremer, O. Meyer, R. Huber, in Handbook of Metalloproteins, A. Messerschmidt, R. Huber, T. Poulos, K. Wieghardt Eds. J. Wiley and Sons Ltd., 2001, p. 1136; H Dobbek, V. Svetlitchnyi, L. Gremer, R. Huber, O. Meyer, Science, 2001, 293, 1281].

It is now clear that many 18 electron organometallic CO derivatives are stable under physiological conditions. On the other hand, a general property of these complexes is their decomposition and accelerated CO release under light irradiation and under oxidative conditions. It is well known that oxygen based radicals are generated in inflammatory processes and that they play a crucial role in the pathogenesis of atherosclerosis. Thus, organometallic carbonyl derivatives release CO in inflamed tissues and atheriosclerotic lesions. This line of thought led to the discovery of three different classes of organometallic drugs.

Class 1—CO Containing Organometallic Complexes Dissolved in Physiologically Compatible Supports This class of compounds comprises either simple 18 electron organometallic carbonyl complexes or modifications thereof designed to improve either their solubility in physiological media or their compatibility with membranes and biomolecules or tissues. The metals that may be used include first transition row biologically active metals (V, Cr, Mn, Fe, Co, Ni, Cu) as well as second (Mo, Ru, Rh, Pd) and third row elements (W, Re, Pt, Au), that appropriately bind the CO ligand. A large number of these compounds bears the cyclopentadienyl ligand (Cp) or derivatives thereof (indenyl, CpR5, and the like) hereby abbreviated as CpR(X), which enable the above-mentioned modifications, and impart some steric protection to the metal center with the corresponding higher reactivity control. The oxidation state of the metal in most of the complexes resembles the one usually found under biological conditions thereby facilitating later metabolization, after CO release.

In the examples listed immediately below, the term "pseudo-halide" is a general name given to mono-anionic ligands isoelectronic with the halides, e.g., thiocyanates, cyanates, cyanides, azides, etc. The term "hydrocarbyl chain" is the general name of a hydrocarbon radical comprising aliphatic $CH_2$ and/or aromatic residues, e.g., $(CH_2)_n$, n=2, 3, etc. or $(CH_2)_n$, $(C_6H_4)_m$, $C_6H_5CH_2$, etc. Alkyl is the general name given to the radical of an aliphatic hydrocarbon chain, e.g. methyl, ethyl, etc. Aryl is the general name given to a radical of an aromatic ring, e.g., phenyl, tolyl, xylyl, etc.

Leading Examples

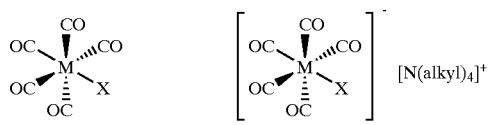

M = Mn, Re
X = Cl, Br, I, alkyl, aryl, acyl, C-glycoside, carboxylate, SR, OR
(R = alkyl, aryl)

M = Cr, Mo, W
X = Cl, Br, I, OR, SR, (R = alkyl, aryl) carboxylate, sugar

-continued

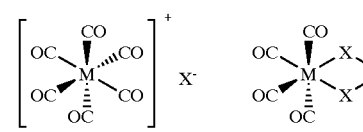

M = Mn, Re
X = halide or weakly coordinating anion

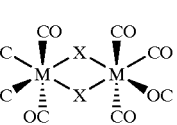

M = Mn, Re
X = halide, SR, OR
R = alkyl, aryl

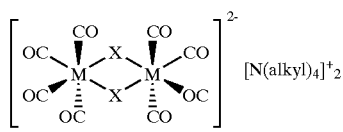

M = Mo, W
X = SR, OR
R = alkyl, aryl
$[N(alkyl)_4]^+{}_2$

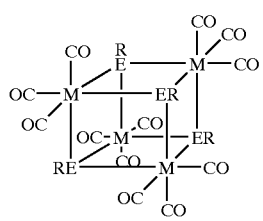

M = Mn, Re
E = S, O
R = H, alkyl, aryl

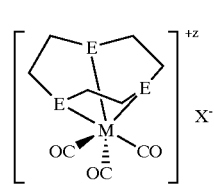

M = Mn, Re (Z = +1); Cr, Mo, W (Z = 0)
E = combinations of N, S and O between 1 to 3 each
X = halide or weakly coordinating anion (for Z = +1)

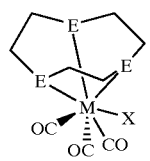

M = Cr, Mo, W
E = combinations of N, S and O between 1 to 3 each
X = halide, pseudohalide, OR, SR, carboxylate, R = alkyl, aryl

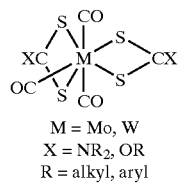

M = Mo, W
X = $NR_2$, OR

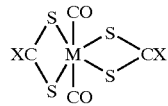

M = Mo, W
X = $NR_2$, OR
R = alkyl, aryl

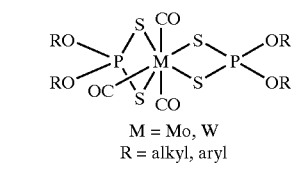

M = Mo, W
R = alkyl, aryl

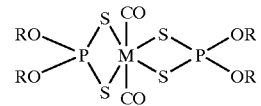

M = Mo, W
R = alkyl, aryl

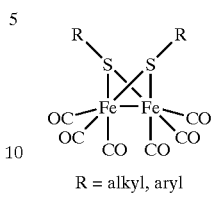

R = alkyl, aryl

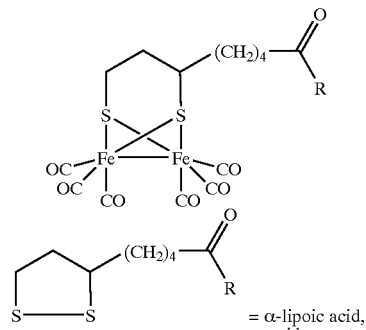

= α-lipoic acid, amide or ester

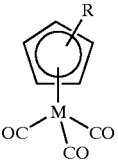

M = Mn, Re

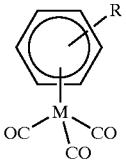

M = Cr, Mo, W

M = Co, Rh

R = H, alkyl, acyl, formyl, carboxylate, sugar, peptide, halide

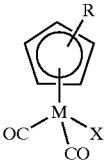

M = Fe, Ru

M = Cr, Mo, W

X = alkyl, aryl, halide, OR', SR', $O_2CR'$, $S_2CNR'_2$, $S_2P(OR')_2$
R' = alkyl, aryl
R = H, alkyl, acyl, formyl, carboxylate, sugar, peptide, halide

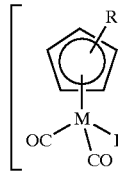

M = Fe, Ru

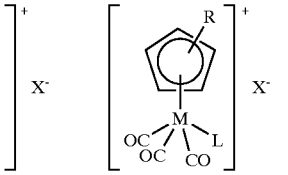

M = Cr, Mo, W

R = H, alkyl, acyl, formyl, carboxylate, sugar, peptide, halide
L = CO, olefin, alkyne, or monodentate 2 electron donor of O, S, N or P
X = halide or weakly coordinating anion

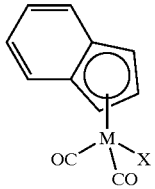

M = Fe, Ru

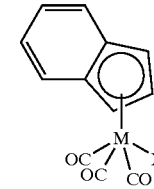

M = Cr, Mo, W

X = alkyl, aryl, halide, OR', SR', $O_2CR'$, $S_2CNR'_2$, $S_2P(OR')_2$
R' = alkyl, aryl

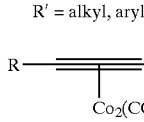

R = H, alkyl, aryl, OR, $CO_2R$

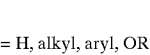

R or R' = H, hydrocarbyl chain
R" = H, alkyl, aryl, OR, $CO_2R$ $[PtCl_2(CO)]_2$     $Au(OSO_2F)(CO)$     MCl(CO)
M = Cu, Au Several modifications can be envisaged to improve higher biological compatibility and solubility. One preferred possibility is to attach carboxylic, peptide or sugar derivatives to the cyclopentadienyl moiety. Examples are depicted for one Mn complex; similar derivatives can be made with compounds containing other metals, as well as for indenyl and other CPR(X) derivatives.

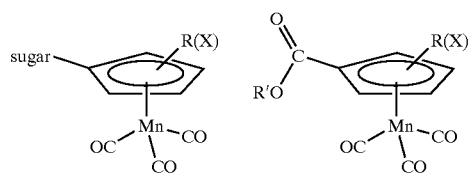

R(X) = H, alkyl, aryl, formyl, acyl, carboxylate or fused C6 aromatic ring (indenyl ligand)
R' = H, alkyl, peptide, sugar Class 2—CO Containing Organometallic Complexes Linked to Other Pharmacologically Important Molecules.

This class of compounds takes advantage of the synergistic effects arising from the combination of two biologically active molecules, which both have beneficial effects. Examples for such drug-drug conjugates have been described in U.S. Pat. No. 6,051,576.

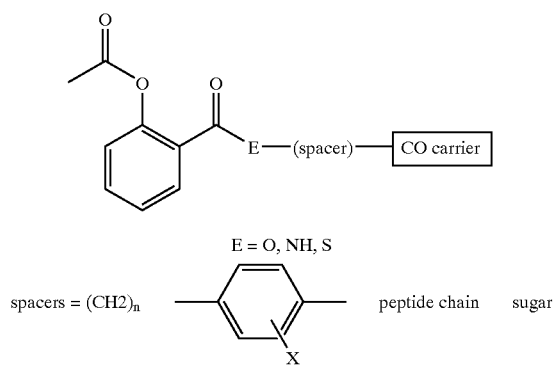

The above mentioned spacers comprise a variety of functions under the following specifications: the value of "n" in the linear hydrocarbon chain is an integer more specifically 1, 2, 3, 4: X is a general symbol for a substituent at the aromatic ring, namely, alkyl, aryl, alkoxy, aryloxl, halogen atom, thiolate; "peptide chain" represents a short chain of natural amino acids ranging from 1 to 4; by "sugars" it is meant the use of a mono-, di- or polysaccharide either protected or modified with adequate protection to increase lipophilicity and/or assure chemical stability of the drug-drug conjugate molecule, for example, with protective groups, such as esters, acetals, and silyl derivatives. The definition of X given immediately above can be extended to carboxylates and amino acids in the cases where X is directly bound to the metal as in some of the leading examples depicted in the next scheme.

Leading Examples

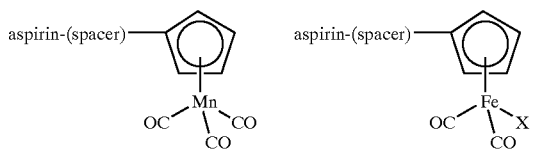

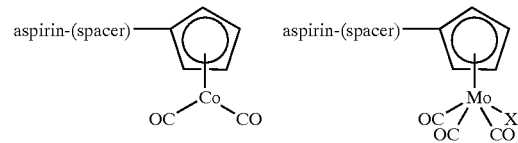

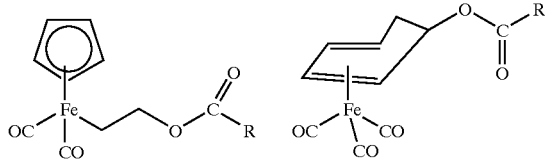

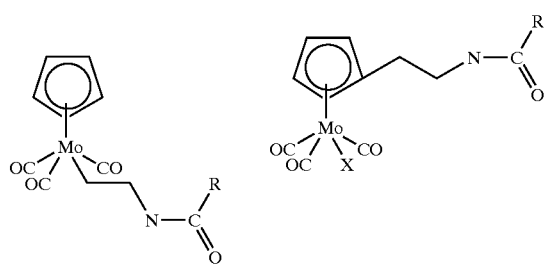

RC(O)O = NSAID drug with carboxylate function, e.g. aspirin, flurbiprofen, naproxen, ibuprofen

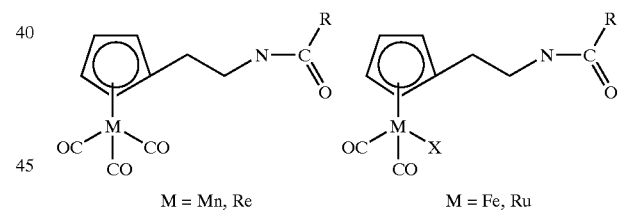

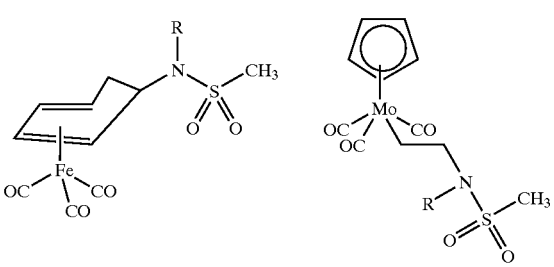

M = Mn, Re        M = Fe, Ru

RC(O)NH = amide of NSAID drug with carboxylate function, e.g. aspirin, flurbiprofen, naproxen, ibuprofen

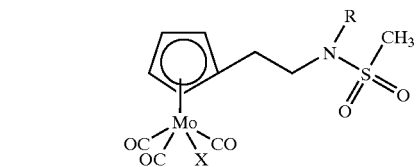

-continued

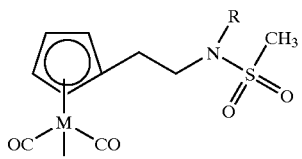

M = Mn, Re

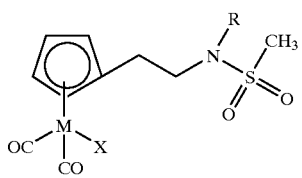

M = Fe, Ru

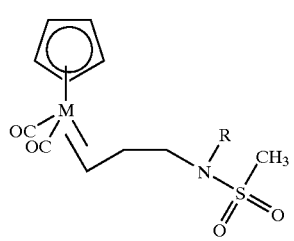

CH$_3$SO$_2$NR = anion of nimesulide, or Cox-2 inhibitors, e.g. NS398, L-745,337

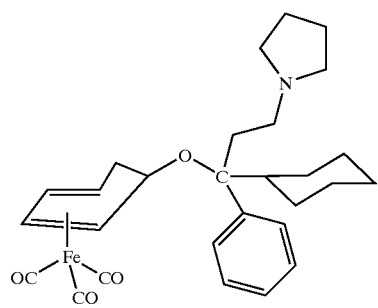

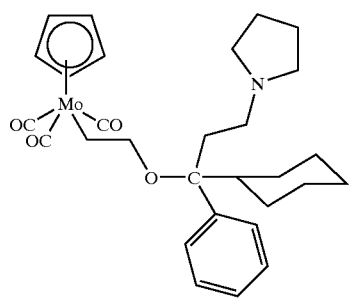

Anticholinergic drugs inter alia Procyclidine derivatives

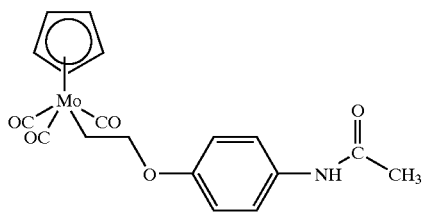

-continued

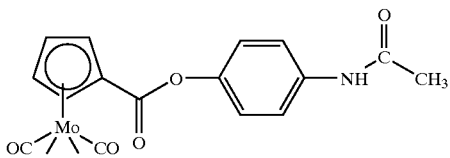

Paracetamol derivatives; X = halide, OR, SR (R= alkyl, aryl)

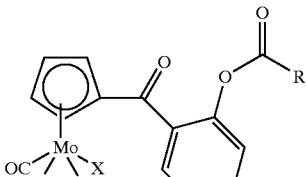

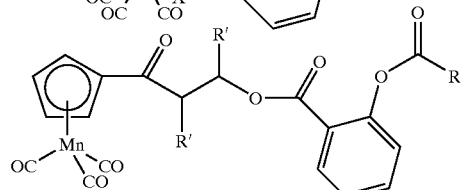

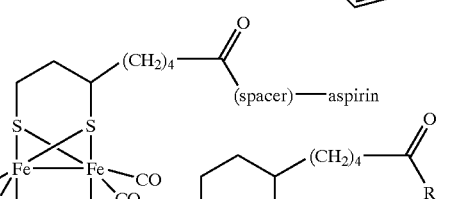

= α-lipoic acid, amide or ester

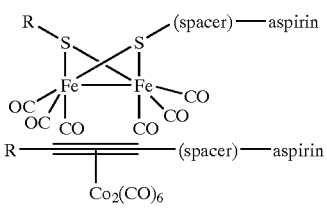

Aspirin derived conjugates. R, R' = alkyl; X = halide, OR, SR

A second group of compounds bears the bioactive molecule, e.g. aspirin, diphosphonate, bound directly to the metal, which can be achieved in several different manners as schematized below for the case of some iron and molybdenum cyclopentadienyl carbonyls, among others. The term "hydrocarbyl chain" is the general name of a hydrocarbon radical comprising aliphatic CH$_2$ and/or aromatic residues, e.g., (CH$_2$)$_n$, n=2, 3, etc. or (CH$_2$)$_n$, (C$_6$H$_4$)$_m$, C$_6$H$_5$CH$_2$, etc.

M = Fe, Ru      M = Cr, Mo, W

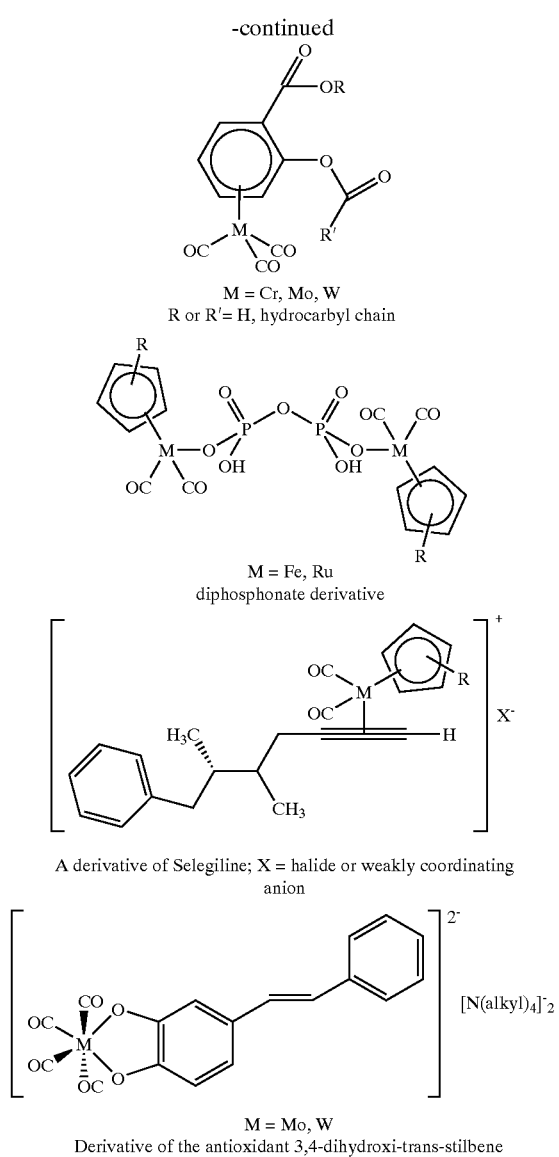

M = Cr, Mo, W
R or R' = H, hydrocarbyl chain

M = Fe, Ru
diphosphonate derivative

A derivative of Selegiline; X = halide or weakly coordinating anion

M = Mo, W
Derivative of the antioxidant 3,4-dihydroxi-trans-stilbene

Class 3: Encapsulated Supramolecular Aggregates Made of CO Containing Organometallic Complexes.

Controlled delivery of drugs into the organism is an important issue, especially in the case of drugs, which have undesired toxic effects if present systemically or at high local concentrations. CO release is a potential problem inasmuch as it can be toxic at high concentrations (see above). For certain applications, a slow release of CO in the blood or in specific target tissues is desirable. Encapsulation within host molecules that are non-toxic is one way to achieve a sustained release of active drugs in the organism. This strategy minimizes the undesired effects that may result from abrupt increases in the concentration and/or availability of a potentially toxic drug.

Cyclodextrins are well known hosts for many drugs and organic molecules and, recently have been applied to host organometallic molecules and enhance their delivery through physiological barriers or membranes. In this respect cyclodextrin has been found to be beneficial for increasing delivery of lipophilic drugs at the skin barrier. [T. Loftsson, M. Masson, Int. J. Pharm. 2001, 225, 15]. Cyclodextrin mediated supramolecular arrangements protect organometallic molecules for prolonged time periods and mask their reactivity, thereby increasing their selectivity towards specific reagents. The hydrophobic part of carbonyl complexes as those exemplified under Class 1 above, fit inside β- or γ-cyclodextrin, or similar structures, with the CO groups facing the reaction medium and the organic ligands buried in the cavity. The resulting reduction in reactivity allows for the extension of the range of therapeutic CO-releasing complexes to cationic and anionic ones. Such charged complexes are more reactive and lose CO faster than the neutral ones when unprotected.

Liposomes and other polymeric nanoparticle aggregates are also useful carriers to target the delivery of CO-releasing organometallic complexes and the combined use of cyclodextrins with such aggregates has been considered as a very promising possibility for drug release. [D. Duchêne, G. Ponchel, D. Wouessidjewe, Adv. Drug Delivery Rev. 1999, 36, 29.]

Conceptual Examples

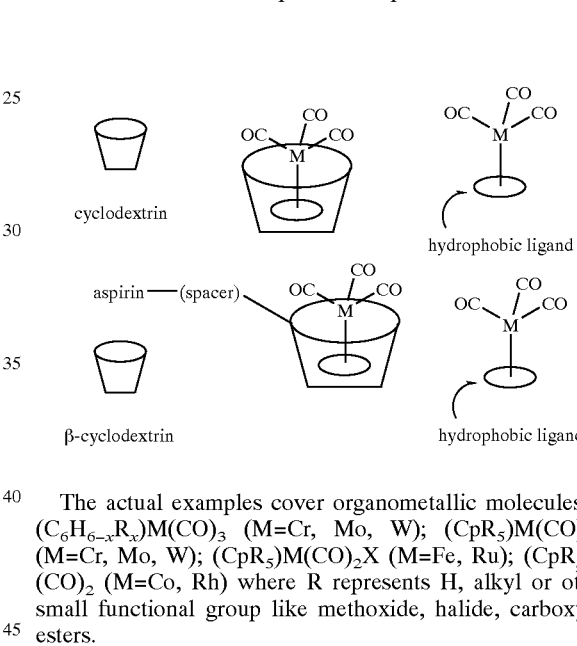

cyclodextrin hydrophobic ligand aspirin —(spacer)

β-cyclodextrin hydrophobic ligand

The actual examples cover organometallic molecules as $(C_6H_{6-x}R_x)M(CO)_3$ (M=Cr, Mo, W); $(CpR_5)M(CO)_3X$ (M=Cr, Mo, W); $(CpR_5)M(CO)_2X$ (M=Fe, Ru); $(CpR_5)M(CO)_2$ (M=Co, Rh) where R represents H, alkyl or other small functional group like methoxide, halide, carboxylic esters.

CO is generated in vivo in a mammal by administering to the mammal a compound comprising a supramolecule aggregate comprised of cyclodextrin and a CO-containing organometallic complex of the formula $(C_6H_{6-x}R_x)M(CO)_3$, where (M=Cr, Mo, W); $(CpR_5)M(CO)_3X$, where (M=Cr, Mo, W); $(CpR_5)M(CO)_2X$, where (M=Fe, Ru); or $(CpR_5)M(CO)_2$, where (M=Co. Rh); where Cp is cyclopentadienyl, R represents H, alkyl, methoxide, halide or a carboxylic ester, subscript x is an integer from 1 to 6, X is alkyl, aryl, halide. OR', SR', $O_2CR'$, $S_2CNR'_2$, or $S_2P(OR')_2$, and R' is alky or aryl.

Mesoporous materials are chemically inert three dimensional molecules with infinite arrays of atoms creating channels and cavities of well defined pore size. These molecules are well suited to host organic and organometallic molecules in their pores. In the presence of biological fluids, smaller molecules undergoing acid-base and/or polar interactions with the inner walls of the pores slowly displace the included drugs, resulting in a controlled delivery of the active principle. Such aggregates have been prepared from M41S materials using organometallic molecules like those depicted under system 1 above. Examples include MCM-41 (linear tubes) and MCM-48 (cavities and pores)

Class 4—CO Containing Inorganic Complexes Bearing Ligands Containing N and/or S Donors That Function as Reversible CO Carriers.

Classical inorganic complexes bearing macrocyclic ligands on an equatorial plane of an octahedral coordination sphere are known to reversibly bind CO much in the same way as hemoglobin. The capacity to bind CO can be "tuned" by the nature of both the macrocycle and the ancilliary ligand trans to CO. A similar behavior has also been reported for other Fe(II) complexes bearing ligands that are much simpler than the porphyrin macrocycles that are the CO acceptor sites in hemoglobin and other heme containing proteins. In order to develop suitable CO delivering drugs, the later type of non-hemic complexes was chosen to avoid interference with the biological heme carriers, heme metabolism, and potential toxicity of heme or heme-like molecule. The complexes selected bear bidentate N donors (diamines, diglyoximes) or bidentate N,S donors of biological significance, like aminothiols or cysteine. Ancilliary ligands are N donors also of biological significance like imidazole, hystidine, and others. The complexes are soluble in aqueous media.

In the examples immediately below, the term pyridines refers to derivatives of the $C_5H_5N$ ring (pyridine) bearing alkyl (R), alkoxy (OR), carboxy (C(O)OR), nitro ($NO_2$), halogen (X), substituents directly bound to the one or more positions of the C5 carbon ring, e.g. $CH_3C_5H_4N$, $O_2NC_5H_4N$. Amino-thiols refers to compounds bearing both the $NH_2$ (amino) and SH (thiol) functions bound to a hydrocarbon skeleton, e.g. $H_2NCH_2CH_2SH$, $1,2-C_6H_4(NH_2)(OH)$. A similar definition applies to amino alcohols, whereby the SH function is replaced by the OH (alcohol) function. The term amino acids refers to naturally occurring single amino acids coordinated in a bidentate fashion by the $NH_2$ and the COO functions as schematically depicted. Glyoximes are bidentate N donors, bearing either alkyl or aryl substituents on the hydrocarbon chain binding the two N atoms, as depicted in the first example below for a diaryl glyoxime. Diimines present a similar structure whereby the OH groups in the diglyoximes are replaced by alkyl or aryl groups. An extension of this family of ligands includes also 2,2'-bypiridines, e.g., 2,2'-dipyridyl, and phenanthrolines.

Leading Examples

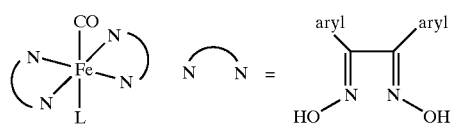

L = N ligand, e.g. imidazole, hystidine, nicotine, pyridines

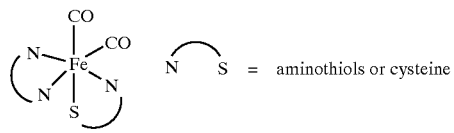

N S = aminothiols or cysteine

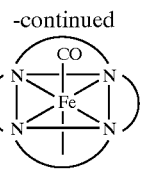

Iron macrocyclic complexes

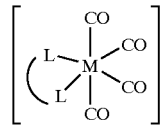

M = Cr, Mo, Mn, Re

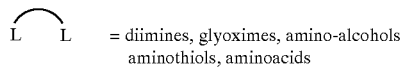

= diimines, glyoximes, amino-alcohols aminothiols, aminoacids

Class 5—CO Containing Inorganic Complexes Bearing Ligands Containing N and/or S Donors that Function as Reversible CO Carriers, Modified by Linkage to Other Pharmacologically Important Molecules.

Following the lines of thought outlined above for Class 2 compounds, new CO carriers of the type described as Class 4, but modified by linking the ligands to other biologically active molecules via an appropriate spacer, were prepared.

Leading Examples

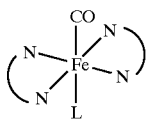

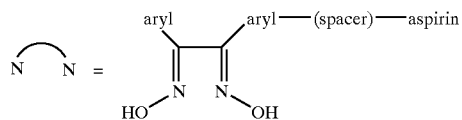

L = N ligand, e.g. imidazole, hystidine, nicotine, pyridines

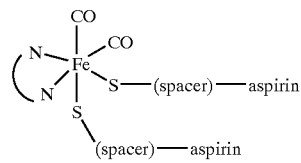

N N = diamines

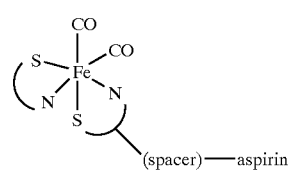

N S = aminothiols or cysteine

Class 6—Organic Substances That Release CO Either by an Enzymatic Process or by Decarbonylation.

In spite of the fact that decarbonylation is not a very common type of reaction in organic chemistry, some organic substances are known to liberate CO upon treatment with either bases, acids, or radical initiators depending on their nature. These substances fall into the following groups: polyhalomethanes of the general form $CH_nX_yX'_{4-(n+y)}$ (X and or X'=F, Cl, Br, I) trichloroacetic acid, and its salts, organic and inorganic esters and sulfinates thereof, triaryl carboxylic acid, formic acid, oxalic acid, α-hydroxyacids and α-ketoacids, esters and salts thereof, under acid conditions; trialkyl and trialkoxybenzaldehydes under acid catalysis; aliphatic aldehydes with radical initiators, e.g., peroxides or light. For the polyhalomethanes, the values of n and y vary in the following way: for n=0, y=1, 2, 3, 4; for n=1, y=1, 2, 3; for n=2, y=1, 2; for n=3, y=1. In the above examples, the term "salt" applies to the ionic derivative of the conjugate base of a given protonic acid, namely a carboxylate, with a main group element ion, namely $Na^+$, $K^+$. Alkyl is the general name given to the radical of an aliphatic hydrocarbon chain, e.g. methyl, ethyl, propyl, butyl, etc. The alkyl group can be branched or straight chain. Aryl is the general name given to a radical of an aromatic ring, e.g., phenyl, tolyl, xylyl, etc. The aryl group will typically have about 6 to about 10 carbon atoms. Ester is the general name given to the functional group —C(O)OR (where R=alkyl, aryl).

The first two categories produce dichlorocarbene, which, under physiological conditions, will be metabolized to CO. In the case of dichloromethane, cytochrome P-450 has been shown to be responsible for the liberation of CO in vivo.

The third group of compounds releases CO under acid catalysis and is sensitive to the aryl substitution pattern. Most likely this is also true for the fourth group which includes trialkyl and triaryl substituted aldehydes. Strong activating groups on the aryl ring favor CO liberation under acid conditions. More importantly, the radical initiated decomposition of aliphatic aldehydes, induced by peroxides or light, produces CO under very mild conditions. The value of "n", the number of substituents (alkyl, aryl, alkoxy, aryloxy) on the aromatic ring, can vary from 0 to 5, preferably 1, 2, or 3.

Leading Examples

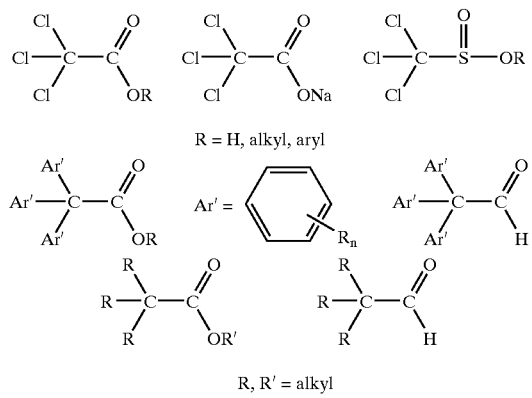

R = H, alkyl, aryl

R, R' = alkyl

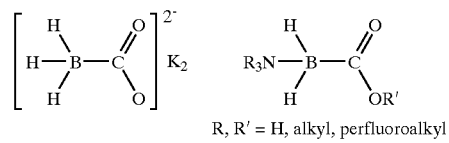

R, R' = H, alkyl, perfluoroalkyl

Class 7—Encapsulated Organic Substances that Release CO Either by an Enzymatic Process or by Decarbonylation.

This system comprises the same molecules described under Class 6, but includes their encapsulation in host-guest supermolecules, liposomes, cyclodextrins, and other polymeric materials that are able to produce nanoencapsulated drug delivery vectors.

Properties of the compounds of the inventions are evaluated by methods known by the one skilled in the art. For example, anti-inflammatory activity can be determined by the method described by Winter et al. (*Proc. Soc. Exp. Biol. Med.* 111, 544, 1962) or by Patrono et al. (*Thrombosis Res.* 17, 317, 1980).

Drug Formulations

Compounds useful in the practice of this invention can be formulated into pharmaceutical compositions together with pharmaceutically acceptable carriers for oral administration in solid or liquid form, or for intravenous, intramuscular, subcutaneous, transdermal, or topical administration. Carriers for oral application are preferred.

Pharmaceutically acceptable carriers for oral administration include capsules, tablets, pills, powders, troches, and granules. In the case of solid dosage forms, the carrier can comprise at least one inert diluent such as sucrose, lactose or starch. Such carriers can also comprise, as is normal practice, additional substances other than diluents, e.g. lubricating agents such as magnesium stearate. In the case of capsules, tablets, troches and pills, the carrier can also comprise buffering agents. Carriers, such as tablets, pills and granules, can be prepared with enteric coatings on the surfaces of the tablets, pills or granules. Alternatively, the enteric coated compounds can be pressed into tablets, pills, or granules. Pharmaceutically acceptable carriers include liquid dosage forms for oral administration, e.g. emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring agents.

Pharmaceutically acceptable carriers for topical administration include DMSO, alcohol or propylene glycol and the like that can be employed with patches or other liquid retaining material to hold the medicament in place on the skin. New approaches based on nanoparticles, nanoencapsulates and the like are also considered convenient for the protection of the active principle and its slow release in the organism or specific tissues.

Pharmaceutically acceptable carriers for intravenous administration include solutions containing pharmaceutically acceptable salts or sugars.

Pharmaceutically acceptable carriers for intramuscular or subcutaneous injection include salts, oils, or sugars.

When used in its acid form, a compound of the present invention can be employed in the form of a pharmaceutically acceptable salt of the acid. Carriers such as solvents, water, buffers, alkanols, cyclodextrins and aralkanols can be used.

Other auxiliary, non-toxic agents may be included, for example, polyethylene glycols or wetting agents.

The pharmaceutically acceptable carriers and compounds described in the present invention are formulated into unit dosage forms for administration to the patients. The dosage levels of active ingredients (i.e. compounds of the present invention) in the unit dosage may be varied so as to obtain an amount of active ingredient that is effective to achieve a therapeutic effect in accordance with the desired method of administration. The selected dosage level therefore mainly depends upon the nature of the active ingredient, the route of administration, and the desired duration of treatment. If desired, the unit dosage can be such that the daily requirement for an active compound is in one dose, or divided among multiple doses for administration, e.g. two to four times per day.

Preferably, the compounds are administered orally once a day. The preferred dose levels will be determined in animals for representative compounds from each class. All compounds described in the present invention generate CO after administration to the body. Although CO is generated preferentially at the sites of inflammation, some of the CO generated will bind to hemoglobin in red blood cells. Thus, dose finding studies will initially be guided by measurement of carboxyhemoglobin (COHb) levels in the blood. Methods for the measurement of COHb levels in the blood are well known and are being used on a regular basis in diagnostic laboratories. In normal healthy humans COHb levels are about 0.5% in healthy nonsmokers and up to 9% in smokers. Preferred dose levels of the compounds described in the present invention are such that no significant rise in COHb levels is observed. However, in some applications a transient rise in COHb levels up to 10% may be tolerated. This level of COHb is not associated with any symptoms.

Compounds in Classes 1 and 4 are administered in a dosage ranging between 5 and 25 mmol/day depending on the nature of the CO containing compound and its molar CO content. The same range of dosage of the CO containing molecule is applied for Class 3 compounds. For aspirin conjugates in classes 2 and 5, the dose can vary from a lower 120 mg/day up to 10 g day with preferred values in the range of 1 g/day for adults. These are indicative values dependent on the nature of the CO carrier molecular fragment and comply with the usual ranges for aspirin dosage. For the polyhalomethane and similar compounds in Class 6, e.g., dichloromethane, the dose range varies between 0.01 to 10 mmol/kg per os, with a preferred dose level of 0.1 mmol/kg. The same range of dosage of active principle is applied in the Class 7 compounds.

The present invention is further illustrated by the examples depicted in the following scheme, which are illustrative only.

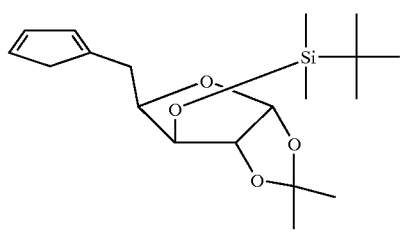

1

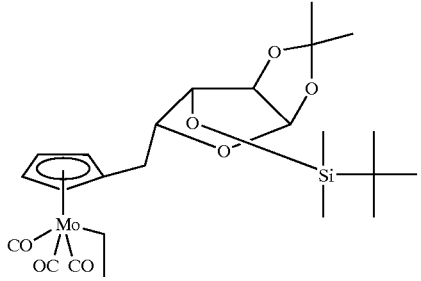

2

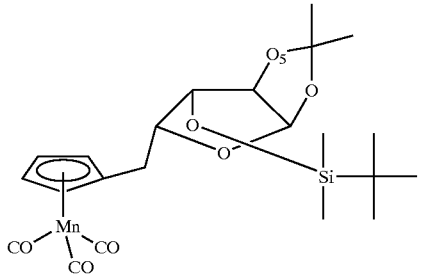

3

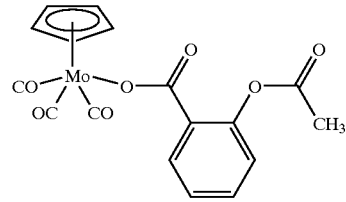

4

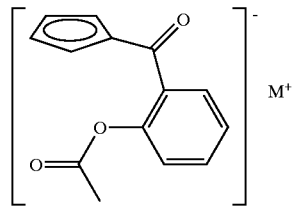

5

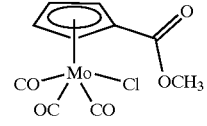

6

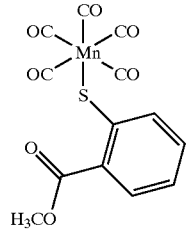

7

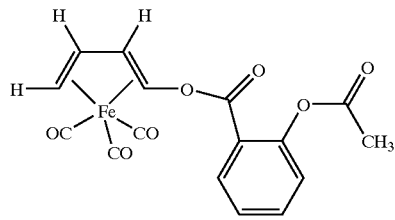

8

-continued

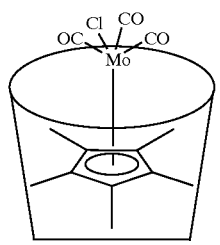

Example 1

Preparation of the Sugar Derivatized Cyclopentadiene Ligand 1

To a solution of CpNa (2.2 g, 24.3 mmol) in DMF (8 ml) was added a solution of the protected sugar (3.7 g, 8.1 mmol) in DMF (20 ml) at −30° C. The reaction mixture was stirred at low temperature for 15 min and then was allowed to warm up to room temperature and stirred for a further 2 h. Destilled water (40 ml) was added to the mixture to destroy the excess of CpNa. The mixture was extracted with dichloromethane (2×100 ml) and the organic layer was dried with $Na_2SO_4$ and DMF was evaporated under vacuum. The residue was purified by columm chromatography on silica (AcOEt/n-hexane 1:8) to give the tittle compound 1 as a yellow oil. Yield g (75%). Since several isomers are present, the compound was best characterized and stabilized by transformation into its $Tl^+$ salt by action of $TlOC_2H_5$ or the $Na^+$ salt by action of NaH. The ionic derivative of cyclopentadiene 1 as the $Tl^+$ salt, hereby abbreviated as $Cp^sTl$, was easily obtained in analyticaly pure form. Anal. Calc. For $C_{19}H_{31}SiO_4Tl$: C,41.12; H, 5.41. Found: C, 40.71; H, 5.29

From the cyclopentadiene ligand 1, other Class 1 cyclopentadienyl complexes bearing sugar substituents on the ring are prepared by standard organometallic procedures as in Example 2 below for a xylose-protected derivative.

From the anion of the cyclopentadiene derivative 1, hereby abbreviated to CpS, prepared either as the $Tl^+$ salt by action of $TlOC_2H_5$ or as the $Na^+$ salt by action of NaH, a wide variety of Class 1 cyclopentadienyl complexes bearing sugar substituents on the ring are prepared by standard organometallic procedures as in Example 3 below.

Example 2

Preparation of Compound 2

To a solution of $Mo(CO)_3(NCMe)_3$ (0.4 g, 1.14 mmol) in toluene (20 ml) was added a solution of $Cp^sH$ (0.4 g, 1.14 mmol) in toluene (20 ml) at room temperature. The reaction mixture was stirred for 2 h and the orange solution was filtered through Celite. The filtrate was concentrated to dryness and the residue was dissolved in dichloromethane (50 ml). Solid $CHI_3$ (0.37 g, mmol) was added to the dichloromethane solution and the colour immediately turned to a deep red. The reaction mixture was stirred for a further 30 min to ensure completion of the reaction and the solvent was removed under vacuum. The title compound 3 was isolated as a red solid. Yield (68%). Anal. Calc. for $C_{22}H_{31}MoO_7SiI$: C, 40.13; H, 4.75. Found: C, 39.84; H, 4.45. Selected IR (KBr, cm$^{-1}$): 2039, 1963, 1884, vs, v(CO);

Example 3

Preparation of Compound 3

Solid $MnBr(CO)_5$ (0.14 g, 0.54 mmol) was added as a solid to a stirred solution of $Cp^sTl$ (0.3 g, 0.54 mmol) in THF (40 ml) at room temperature. The reaction mixture was stirred for 16 h and the solvent was removed under vacuum. The residue was extracted in dichloromethane to yield the title compound 2 as a waxy yellow solid. Yield g (73%). Anal. Calc. for $C_{22}H_{31}MnO_7Si$: C, 53.98; H, 6.32. Found: C, 53.51; H, 6.15. Selected IR (KBr, cm$^{-1}$): 2019, 1928, vs, v(CO).

Example 4

Preparation of Compound 4

Dichloromethane (20 ml) was added to a mixture of $(C_5H_5)Mo(CO)_3Cl$ (0.40 g, 1.42 mmol) and silver salt of the o-acetylsalycilic acid (0.40 g, 1.42 mmol) and the reaction mixture was stirred for 2 h. at room temperature. The white precipitate of AgCl was separated by filtration and the filtrate was concentrated to dryness to yield compound 4 in 85% yield (0.51 g). Anal. Calc. for $C_{17}H_{12}O_7Mo$: C, 48.12; H, 2.83; Found: C, 47.90; H, 2.76.

Example 5

Preparation of the Aspirin Derivatized Cyclopentadienyl Ligand 5

To a mixture of CpTl (1 g, 3.71 mmol) and acetylsalicyloyl chloride (0.73 g, 3.71 mmol) toluene was added (30 ml). The reaction mixture was stirred overnight at room temperature. The solution was filtered through celite and the filtrate was concentrated to dryness to yield the cyclopentadiene derivatized with aspirin as a white solid in 82% yield (0.69 g). Since several isomers are present the compound is best characterized as its Tl derivative. This is prepared by dissolving the compound in tetrahydrofuran (30 ml) treating it with $TlOC_2H_5$. A yellow precipitate of 5$^-$ as the $Tl^+$ salt was immediately formed in 77% yield.

From 5Tl or its Na analogs, prepared by replacement of $TlOC_2H_5$ with NaH, a variety of compounds can be made, using straightforward organometallic chemistry methods, that contain the aspirin bound to the cyclopentadienyl ring.

Example 6

Preparation of Compound 6

$[BU_4N][Mo(CO)_5I]$ (0.96 g; 1.60 mmol) and [Cp (COOMe)]Na (0.28 g; 1.90 mmol) are dissolved in 20 mL THF each. The 2 solutions are mixed in a reaction flask and refluxed overnight (18 hours). The yellow brown solution is evaporated under vacuum and an oily residue is obtained. This is treated with 20 mL ether, 20 mL distilled water and 0.1 mL acetic acid. After 20 min of stirring, 5 mL of $CCl_4$ are added and the colour of the emulsion turns to red. The mixture is stirred for further 20 min and the ether phase is separated. The remaining aqueous phase is extracted with ether (5×20 mL). The ether extracts are combined and evaporated under vacuum. The red residue is redissolved in 20 mL of acetone, then some active charcoal and anhydrous $Na_2SO_4$ are added. The mixture is stirred for 30 min and then filtered with a canula. The red filtrate is evaporated to dryness and washed with cold hexane. Yield (based on [$Me_4N$][$Mo(CO)_5I$]): 41%. Anal. Calc. for $C_{10}H_7ClMoO_5$ (338.56): C 35.48; H 2.08. Found: C 35.83; H 2.50. Selected IR (KBr/cm$^{-1}$): ν=2058 (s), 1961 (s), 1974 (s), 1856 (w), 1725 (s), $^1$H NMR ($CDCl_3$, 300 MHz, r,t): δ=6.04–6.02 (m, 2H, Cp-$H_{3,4}$); 5.74–5.69 (m, 2H, Cp-$H_{1,5}$); 3.83 (s, 3H, $H_{COOCH_3}$).

Example 7

Preparation of Compound 7

The sodium salt $NaSC_6H_4C(O)OMe$ was prepared in the following way: to 1.66 mL of $HSC_6H_4C(O)OMe$ (2.035 g; 12.097 mmol) THF (100 mL) was added. The pale yellow solution was cooled to −10° C. and NaH (0.290 g; 95% pure, 1 equivalent) added slowly. The mixture turned into a bright yellow suspension from which a yellow solid precipitated within a few minutes. After 1 hr. the solvent was evaporated and the powder residue dried under vacuum (quantitative yield). $NaSC_6H_4C(O)OMe$ (0.384 g; 2.017 mmol) was charged into a schlenk tube and THF (30 mL) added. The yellow suspension was cooled to 0° C., and $Mn(CO)_5Br$ (0.554 g; 2.017 mmol) was added slowly in the solid state. The reaction mixture immediately turned green and progressively became yellow. Stirring was continued for 18 hours at r.t. after which time the orange suspension was filtered off. The orange solution was cooled at −30° C. and a small amount of an impurity precipitated. This was filtered off and the solution evaporated to dryness, yielding [$Mn(CO)_5$($SC_6H_4C(O)OMe$] in 80% yield. Anal. Calc for $C_{13}H_7MnO7S$:C, 43.11; H, 1.95; S, 8.85. Found: C, 42.87; H, 1.84; S, 8.26. Selected IR (KBr, cm$^{-1}$): 2046 (m), 1994 (s), 1928 (s)1904 (s); 1708 (m). $^1$H NMR (acetone d$^6$; 300 MHz): 8.53 (d,1H,3J=7.8 Hz, SCH); 7.40–7.31 (m,2H, $C_6H_4$); 7.21 (dd, 1H, $C_6H_4$); 3.96 (s, 3H,$CH_3$)

Example 8

Preparation of Compound 8

A solution of acetylsalicyoyl chloride (1.1 g; 1.1 equivalent) in dichloromethane (15 mL) was added dropwise to a solution of trans,trans-2,4-hexadiene-1-ol (0.574 g; 5.1 mmol) also in dichloromethane (15 mL) and triethylamine (4 mL) at 0° C. After overnight stirring at r.t. the mixture was evaporated to dryness. The residue was taken up in ethyl acetate and extracted with water. The organic phase was dried over sodium sulfate, filtered and evaporated to dryness. The crude product was purified by column chromatography using ethyl acetate/n-hexane (1:5) as eluent. After evaporation, the trans,trans-2,4-hexadiene-1-oxi ester of the acetylsalicylic acid was obtained as an oil (0.99 g; 75% yield). $^1$H NMR ($CDCl_3$; 300 MHz): 7.95 (d,1H,J=7.8 Hz, Harom); 7.49–7.44 (m, 1H, Harom); 7.22 (t,1H,J=7.5 Hz, J=7.5 Hz, H arom); 7.01 (d, 1H, J=8.1 Hz, H arom); 6.28–6.20 (m, 1H, H diene); 5.99 (t, 1H, J=14.4 Hz, J=11.4 Hz, H diene); 5.76–5.58 (m 2H, H diene); 4.71 (d, 2H, J=6.6 Hz, $CH_2$); 2.24 (s, 3H, $CH_3OAc$); 1.69 (d, 3H, J=6.6 Hz, $CH_3$).

A solution of this diene ester (0.4 g; 1.54 mmol), $Me_3NO$ (0.3 g; 2 equivalents) and $Fe(CO)_5$ (0.20 mL; 1 equivalent) in THF was stirred at r.t. overnight. The resulting mixture was filtered, and evaporated to dryness to give a dark red oil of compound 8 (0.39 g; 62% yield). IR (KBr pellet, cm$^{-1}$): 2046 (s), 1954 (s), 1928 (s), 1770 (s), 1722 (s). $^1$H NMR ($CD_3OD$); 300 MHz): 7.94–7.91 (m,1H, H arom); 7.58–7.52 (m, 1H, Harom); 7.32–7.27 (m, 1H, H arom); 7.09–7.07 (m, 1H, H arom); 6.30–6.25 (m, 1H, H diene); 6.04–6.01 (m, 1H, H diene); 5.77–5.62 (m, 2H, H diene); 4.69 (d, 2H, J=6.0 Hz, $CH_2$); 2.20 (s, 3H, $CH_3OAc$); 1.70 (d, 3H, J=6.0 Hz, $CH_3$).

Example 9

Preparation of β-CD/Cp*Mo(CO)$_3$Cl 6

A solution of β-CD hydrate (1.36 g, 1.20 mmol) in water (18.5 ml) was treated with a solution of CP*MO(CO)$_3$Cl (0.42 g, 1.20 mmol) in $CH_2Cl_2$ (8 ml) and the mixture kept at 60° C. for 6 h. After evaporation of the $CH_2Cl_2$ and addition of ethanol (4 ml), the mixture was stirred for 12 h at room temperature. The suspension was filtered and the pale red powder washed several times with $CH_2Cl_2$, water and vacuum dried. Yield: 80%

In summary, various effects of CO have been demonstrated, however, the ways the amount of CO can be increased in the body remain limited. Thus, this invention includes several embodiments to alleviate this problem. One embodiment is directed to a new way of administration of CO by means of compounds having ability to release CO either because they comprise CO (Classes 1, 2, 3, 4, and 5) or because they are able to generate CO (classes 6 and 7). The preferred use of these compounds (that is any compound having the ability to release CO) is as an anti-inflammatory agent. However, releasing of CO may be used for other indications. Among the compounds of the invention, all are not already known. The new compounds include those comprising complexes linked to another pharmacologically important molecule (Classes 2 and 5).

What is claimed is:

1. A method for treating a disease in a mammal selected from the group consisting of an inflammatory disease, a disease with a strong inflammatory component, asthma, injury, infarction, and a circulatory disease, wherein said method comprises the step of delivering to said mammal a safe and effective amount of a compound having the ability to release CO in vivo by spontaneous or metabolic process, wherein said compound is a CO containing organometallic complex in a cyclodextrin host that encapsulates at least a portion of the complex or an aggregate of a CO containing organometallic complex and liposome.

2. The method of claim 1, wherein said compound contains a moiety having the ability to release CO in vivo.

3. The method of claim 1, wherein said compound is combined with a carrier and/or a second pharmaceutically important molecule.

4. The method of claim 3, wherein said second pharmaceutically important molecule is an anti-inflammatory agent.

5. The method of claim 4, wherein said anti-inflammatory agent is a cyclooxygenase inhibitor or a phosphodiesterase inhibitor.

6. The method of claim 5, wherein said cyclooxygenase inhibitor is selected from the group consisting of aspirin, nimesulide, and naproxen.

7. The method of claim 3, wherein said second pharmaceutically important molecule is a biphosphonate.

8. The method of claim 1, wherein said disease with a strong inflammatory component is atherosclerosis, stroke, coronary disease, or Alzheimer's disease.

9. The method of claim 1, wherein said inflammatory disease is a chronic inflammatory disease.

10. The method of claim 9, wherein said chronic inflammatory disease is rheumatoid arthritis.

11. The method of claim 1, wherein said mammal is a human.

12. A method for generating CO in vivo in a mammal, wherein said method comprises administering to said mammal a safe and effective amount of a compound comprising a supramolecule aggregate comprised of cyclodextrin and a CO-containing organometallic complex of the formula $(C_6H_{6-x}R_x)M(CO)_3$, where (M=Cr, Mo, W); $(CpR_5)M(CO)_3X$, where (M=Cr, Mo, W); $(CpR_5)M(CO)_2X$, where (M=Fe, Ru); or $(CpR_5)M(CO)_2$, where (M=Co, Rh); where $CpR_5$ represents indenyl, R represents H, alkyl, methoxide, halide or a carboxylic ester, subscript x is a positive integer equal to 6 or less, X is alkyl, aryl, halide, OR', SR', $O_2CR'$, $S_2CNR'_2$, or $S_2P(OR')_2$, and R' is alkyl or aryl.

13. The method of claim 12, wherein the cyclodextrin is β-cyclodextrin.

14. The method of claim 12, wherein the cyclodextrin is γ-cyclodextrin.

* * * * *